US006992237B1

(12) United States Patent
Habben et al.

(10) Patent No.: US 6,992,237 B1
(45) Date of Patent: Jan. 31, 2006

(54) REGULATED EXPRESSION OF GENES IN PLANT SEEDS

(75) Inventors: Jeffrey E. Habben, Urbandale, IA (US); Chris Zinselmeier, Grimes, IA (US); Dwight T. Tomes, Van Meter, IA (US)

(73) Assignee: Pioneer Hi-Bred International Inc., Johnston, IA (US)

( * ) Notice: Subject to any disclaimer, the term of this patent is extended or adjusted under 35 U.S.C. 154(b) by 0 days.

(21) Appl. No.: 09/545,334

(22) Filed: Apr. 7, 2000

Related U.S. Application Data

(60) Provisional application No. 60/129,844, filed on Apr. 16, 1999.

(51) Int. Cl.
  *C12N 15/29* (2006.01)
  *C12N 15/82* (2006.01)
  *C12N 15/87* (2006.01)
  *A01H 5/00* (2006.01)

(52) U.S. Cl. ...................... 800/298; 800/278; 800/293; 800/294; 800/287; 536/23.1; 536/23.6; 536/24.1; 435/468

(58) Field of Classification Search ................ 435/486, 435/470, 410, 419, 430, 320.1, 468; 536/23.1, 536/24.1, 23.6; 800/278, 287, 290, 292, 800/293, 298, 294
See application file for complete search history.

(56) References Cited

U.S. PATENT DOCUMENTS

| 4,943,674 | A | | 7/1990 | Houck et al. | |
|---|---|---|---|---|---|
| 5,177,307 | A | * | 1/1993 | Houck et al. | ............... 800/205 |
| 5,780,709 | A | | 7/1998 | Adams et al. | |
| 5,877,400 | A | * | 3/1999 | Tomes et al. | ............... 800/205 |
| 6,229,066 | B1 | | 5/2001 | Morris | |

FOREIGN PATENT DOCUMENTS

| WO | WO 91/01323 | 2/1991 |
|---|---|---|
| WO | WO 93/07272 | 4/1993 |
| WO | WO 96/29858 | 10/1996 |
| WO | WO 99/06571 | 2/1999 |

OTHER PUBLICATIONS

Takei et al (2001, Journal of Biological Chemistry 276(28): 26405-26410).*
Kusaba et al (1998, Plant Physiology 116(2):471-476).*
Binns (1994, Annu. Rev. Plant Physiol. Plant Mol. Biol. 45:173-196).*
Oommenn et al (1994, The Plant Cell 6:1789-1803).*
The Arabidopsis Genome Initiative, Nature 408(Dec. 14): 796-815, 2000.*
Houba-Herin, N., et al. *The Plant Journal* 17(6), 615-626 (1999), "Cytokinin oxidase from *Zea Mays*: purification, cDNA cloning and expression in moss protoplasts".

Rinaldi, A.C. and Comandini, O., *Trends in Plant Science* v.4 (4), 127-128 (1999), "Cytokinin oxidase: new insight into enzyme properties".
Morris, R.O., et al. (1999) GenBank, Accession AF044603, "Isolation of a gene encoding a glycosylated cytokinin oxidase from maize".
Cheikh, N. and R.J. Jones. *Plant Physiol.* 106:45-51 (1994), "Disruption of maize kernel growth and development by heat stress".
Dietrich, J., et al. *Plant Physiol. Biochem.* 33(3)327-336 (1995), "Changes in cytokinins and cytokinin oxidase activity in developing maize kernels and the effects of exogenous cytokinin on kernel development".
Gan, S., and R.M. Amasino. *Science* 270:1986-1988 (1995), "Inhibition of leaf senescence by autoregulated production of cytokinin".
Lejeune, P., et al. *Aust. J. Plant Physiol.* 25:481-488 (1998), "Hormonal control of ear abortion in a stress-sensitive maize (*Zea mays*) inbred".
Morris, R. O., et al. *Biochemical and Biophysical Research Communications* 255:328-333 (1999), "Isolation of a gene encoding a glycosylated cytokinin oxidase from maize".
Riou-Khamlichi, C., et al. *Science* 283:1541-1544 (1999), "Cytokinin activation of *Arabidopsis* cell division through a D-type cyclin".
Jones, R.J., and B. M. N. Schreiber. *Plant Growth Regulation* 23(1-2):123-134 (1997), "Role and function of cytokinin oxidase in plants".
Vantoai, et al., "Improved biomass production and abiotic stress tolerance of transgenic arabidopsis containing an autoregulated cytokinin biosynthesis gene", 1999, *Plant & Animal Genome VII Conference*.
Roeckel, et al., "Effects of seed-specific expression of cytokinin biosynthetic gene on canola and tobacco phenotypes", 1997, *Transgenic Research*, 6: 133-141.
Ma Qing-Hu, et al., "Seed-specific expression of the isopentenyl transferase gene (ipt) in transgenic tobacco", 1998, *Aust. J. Plant Physiol.*, 25: 53-59.
Roeckel, et al., "Phenotypic alterations and component analysis of seed yield in transgenic *Brassica napus* plants expressing the tzs gene", 1998, *Physiol. Plant*, 243-249.
Kaminek, M., "Progress in cytokinin research", 1992, *Trends in Biotechnology*, 5: 159-164.

* cited by examiner

*Primary Examiner*—Amy J. Nelson
*Assistant Examiner*—Stuart F. Baum
(74) *Attorney, Agent, or Firm*—Pioneer Hi-Bred Int'l Inc.

(57) ABSTRACT

This invention relates generally to the field of plant molecular biology. More specifically, this invention relates to methods and reagents for the temporal and/or spatial expression of genes that affect metabolically effective levels of cytokinins in plant seeds and related maternal tissue. This invention further relates to transgenic plants having enhanced levels of cytokinin expression wherein the transgenic plant exhibits useful characteristics, including: improved seed size, decreased tip kernel abortion, increased seed set during unfavorable environmental conditions, and stability of yield.

17 Claims, 1 Drawing Sheet

Figure 1A
Figure 1B
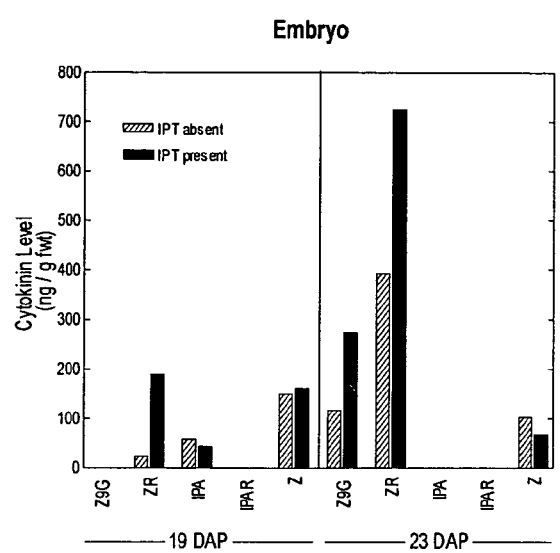
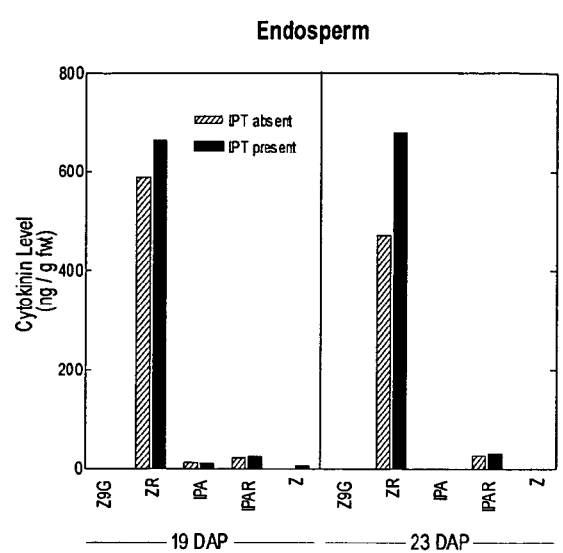

SEQUENCE LISTING

<160> NUMBER OF SEQ ID NOS: 12

<210> SEQ ID NO 1
<211> LENGTH: 1608
<212> TYPE: DNA
<213> ORGANISM: Zea mays
<220> FEATURE:
<221> NAME/KEY: CDS
<222> LOCATION: (1)...(1605)

<400> SEQUENCE: 1

| | | | | | | | | | | | | | | | | |
|---|---|---|---|---|---|---|---|---|---|---|---|---|---|---|---|---|
| atg | gcg | gtg | gtt | tat | tac | ctg | ctg | ctg | gcc | ggg | ctg | atc | gcc | tgc | tct | 48 |
| Met | Ala | Val | Val | Tyr | Tyr | Leu | Leu | Leu | Ala | Gly | Leu | Ile | Ala | Cys | Ser | |
| 1 | | | | 5 | | | | | 10 | | | | | 15 | | |

| cat | gca | cta | gcg | gca | ggc | acg | ctt | gcg | ctc | gga | gaa | gat | cgc | ggc | cgt | 96 |
|---|---|---|---|---|---|---|---|---|---|---|---|---|---|---|---|---|
| His | Ala | Leu | Ala | Ala | Gly | Thr | Leu | Ala | Leu | Gly | Glu | Asp | Arg | Gly | Arg | |
| | | | 20 | | | | | 25 | | | | | 30 | | | |

| ccc | tgg | cca | gcc | ttc | ctc | gcc | gcg | ctg | gcc | ttg | gac | ggc | aag | ctc | cgg | 144 |
|---|---|---|---|---|---|---|---|---|---|---|---|---|---|---|---|---|
| Pro | Trp | Pro | Ala | Phe | Leu | Ala | Ala | Leu | Ala | Leu | Asp | Gly | Lys | Leu | Arg | |
| | | 35 | | | | | 40 | | | | | 45 | | | | |

| acc | gac | agc | aac | gcg | acg | gcg | gcg | gcc | tcg | acg | gac | ttc | ggc | aac | atc | 192 |
|---|---|---|---|---|---|---|---|---|---|---|---|---|---|---|---|---|
| Thr | Asp | Ser | Asn | Ala | Thr | Ala | Ala | Ala | Ser | Thr | Asp | Phe | Gly | Asn | Ile | |
| 50 | | | | | 55 | | | | | 60 | | | | | | |

| acg | tcg | gcg | ctc | ccg | gcg | gcg | gtc | cta | tac | ccg | tcg | tcc | acg | ggc | gac | 240 |
|---|---|---|---|---|---|---|---|---|---|---|---|---|---|---|---|---|
| Thr | Ser | Ala | Leu | Pro | Ala | Ala | Val | Leu | Tyr | Pro | Ser | Ser | Thr | Gly | Asp | |
| 65 | | | | 70 | | | | | 75 | | | | | 80 | | |

| ctg | gtg | gcg | ctg | ctg | agc | gcg | gcc | aac | tcc | acc | ccg | ggg | tgg | ccc | tac | 288 |
|---|---|---|---|---|---|---|---|---|---|---|---|---|---|---|---|---|
| Leu | Val | Ala | Leu | Leu | Ser | Ala | Ala | Asn | Ser | Thr | Pro | Gly | Trp | Pro | Tyr | |
| | | | | 85 | | | | | 90 | | | | | 95 | | |

| acc | atc | gcg | ttc | cgc | ggc | cgc | ggc | cac | tcc | ctc | atg | ggc | cag | gcc | ttc | 336 |
|---|---|---|---|---|---|---|---|---|---|---|---|---|---|---|---|---|
| Thr | Ile | Ala | Phe | Arg | Gly | Arg | Gly | His | Ser | Leu | Met | Gly | Gln | Ala | Phe | |
| | | | 100 | | | | | 105 | | | | | 110 | | | |

| gcc | ccc | ggc | ggg | gtg | gtc | gtc | aac | atg | gcg | tcc | ctg | ggc | gac | gcc | gcc | 384 |
|---|---|---|---|---|---|---|---|---|---|---|---|---|---|---|---|---|
| Ala | Pro | Gly | Gly | Val | Val | Val | Asn | Met | Ala | Ser | Leu | Gly | Asp | Ala | Ala | |
| | | 115 | | | | | 120 | | | | | 125 | | | | |

| gcc | gcc | gcg | ccg | ccg | cgc | gtc | aac | gtg | tcc | gcg | gac | ggc | cgc | tac | gtg | 432 |
|---|---|---|---|---|---|---|---|---|---|---|---|---|---|---|---|---|
| Ala | Ala | Ala | Pro | Pro | Arg | Val | Asn | Val | Ser | Ala | Asp | Gly | Arg | Tyr | Val | |
| | 130 | | | | | 135 | | | | | 140 | | | | | |

| gac | gcc | ggc | ggc | gag | cag | gtg | tgg | atc | gac | gtg | ctg | cgc | gcg | tct | ctg | 480 |
|---|---|---|---|---|---|---|---|---|---|---|---|---|---|---|---|---|
| Asp | Ala | Gly | Gly | Glu | Gln | Val | Trp | Ile | Asp | Val | Leu | Arg | Ala | Ser | Leu | |
| 145 | | | | | 150 | | | | | 155 | | | | | 160 | |

| gcg | cgc | ggc | gtg | gcg | ccg | cgc | tcc | tgg | acc | gac | tac | ctc | tac | ctc | acc | 528 |
|---|---|---|---|---|---|---|---|---|---|---|---|---|---|---|---|---|
| Ala | Arg | Gly | Val | Ala | Pro | Arg | Ser | Trp | Thr | Asp | Tyr | Leu | Tyr | Leu | Thr | |
| | | | | 165 | | | | | 170 | | | | | 175 | | |

| gtc | ggc | ggc | acg | ctg | tcc | aac | gca | ggc | atc | agc | ggc | cag | gcg | ttc | cgc | 576 |
|---|---|---|---|---|---|---|---|---|---|---|---|---|---|---|---|---|
| Val | Gly | Gly | Thr | Leu | Ser | Asn | Ala | Gly | Ile | Ser | Gly | Gln | Ala | Phe | Arg | |
| | | | 180 | | | | | 185 | | | | | 190 | | | |

| cac | ggc | cca | cag | ata | tct | aac | gtg | ctg | gag | atg | gac | gtt | atc | acc | ggc | 624 |
|---|---|---|---|---|---|---|---|---|---|---|---|---|---|---|---|---|
| His | Gly | Pro | Gln | Ile | Ser | Asn | Val | Leu | Glu | Met | Asp | Val | Ile | Thr | Gly | |
| | | 195 | | | | | 200 | | | | | 205 | | | | |

| cat | ggg | gag | atg | gtg | acg | tgc | tcc | aag | cag | ctg | aac | gcg | gac | ctg | ttc | 672 |
|---|---|---|---|---|---|---|---|---|---|---|---|---|---|---|---|---|
| His | Gly | Glu | Met | Val | Thr | Cys | Ser | Lys | Gln | Leu | Asn | Ala | Asp | Leu | Phe | |
| | 210 | | | | | 215 | | | | | 220 | | | | | |

| gac | gcc | gtc | ctg | ggc | ggg | ctg | ggg | cag | ttc | gga | gtg | atc | acc | cgg | gcc | 720 |
|---|---|---|---|---|---|---|---|---|---|---|---|---|---|---|---|---|
| Asp | Ala | Val | Leu | Gly | Gly | Leu | Gly | Gln | Phe | Gly | Val | Ile | Thr | Arg | Ala | |
| 225 | | | | | 230 | | | | | 235 | | | | | 240 | |

| cgg | atc | gcg | gtg | gag | ccg | gcg | ccg | gcg | cgg | gcg | cgg | tgg | gtg | cgg | ctc | 768 |
|---|---|---|---|---|---|---|---|---|---|---|---|---|---|---|---|---|
| Arg | Ile | Ala | Val | Glu | Pro | Ala | Pro | Ala | Arg | Ala | Arg | Trp | Val | Arg | Leu | |
| | | | | 245 | | | | | 250 | | | | | 255 | | |

```
gtg tac acc gac ttc gcg gcg ttc agc gcc gac cag gag cgg ctg acc      816
Val Tyr Thr Asp Phe Ala Ala Phe Ser Ala Asp Gln Glu Arg Leu Thr
    260                 265                 270 gcc ccg cgg ccc ggc ggc ggc gcg tcg ttc ggc ccg atg agc tac          864
Ala Pro Arg Pro Gly Gly Gly Ala Ser Phe Gly Pro Met Ser Tyr
275                 280                 285 gtg gaa ggg tcg gtg ttc gtg aac cag agc ctg gcg acc gac ctg gcg      912
Val Glu Gly Ser Val Phe Val Asn Gln Ser Leu Ala Thr Asp Leu Ala
290                 295                 300 aac acg ggg ttc ttc acc gac gcc gac gtc gcc cgg atc gtc gcg ctc      960
Asn Thr Gly Phe Phe Thr Asp Ala Asp Val Ala Arg Ile Val Ala Leu
305                 310                 315                 320 gcc ggg gag cgg aac gcc acc acc gtg tac agc atc gag gcc acg ctc     1008
Ala Gly Glu Arg Asn Ala Thr Thr Val Tyr Ser Ile Glu Ala Thr Leu
                325                 330                 335 aac tac gac aac gcc acg gcg gcg gcg gcg gtg gac cag gag ctc gcg     1056
Asn Tyr Asp Asn Ala Thr Ala Ala Ala Ala Val Asp Gln Glu Leu Ala
                340                 345                 350 tcc gtg ctg ggc acg ctg agc tac gtg gaa ggg ttc gcg ttc cag cgc     1104
Ser Val Leu Gly Thr Leu Ser Tyr Val Glu Gly Phe Ala Phe Gln Arg
            355                 360                 365 gac gtg tcc tac acg gcg ttc ctt gac cgg gtg cac ggc gag gag gtg     1152
Asp Val Ser Tyr Thr Ala Phe Leu Asp Arg Val His Gly Glu Glu Val
370                 375                 380 gcg ctc aac aag ctg ggg ctg tgg cgg gtg ccg cac ccg tgg ctc aac     1200
Ala Leu Asn Lys Leu Gly Leu Trp Arg Val Pro His Pro Trp Leu Asn
385                 390                 395                 400 atg ttc gtg ccg cgc tcg cgc atc gcc gac ttc gac cgc ggc gtc ttc     1248
Met Phe Val Pro Arg Ser Arg Ile Ala Asp Phe Asp Arg Gly Val Phe
                405                 410                 415 aag ggc atc ttg cag ggc acc gac atc gtc ggc ccg ctc atc gtc tac     1296
Lys Gly Ile Leu Gln Gly Thr Asp Ile Val Gly Pro Leu Ile Val Tyr
                420                 425                 430 ccc ctc aac aaa tcc atg tgg gac gac ggc atg tcg gcg gcg acg ccg     1344
Pro Leu Asn Lys Ser Met Trp Asp Asp Gly Met Ser Ala Ala Thr Pro
            435                 440                 445 tcg gag gac gtg ttc tac gcg gtg tcg ctg ctc ttc tcg tcg gtg gcg     1392
Ser Glu Asp Val Phe Tyr Ala Val Ser Leu Leu Phe Ser Ser Val Ala
450                 455                 460 ccc aac gac ctg gcg agg ctg cag gag cag aac agg agg atc ctg cgc     1440
Pro Asn Asp Leu Ala Arg Leu Gln Glu Gln Asn Arg Arg Ile Leu Arg
465                 470                 475                 480 ttc tgc gac ctc gcc ggg atc cag tac aag acc tac ctg gcg cgg cac     1488
Phe Cys Asp Leu Ala Gly Ile Gln Tyr Lys Thr Tyr Leu Ala Arg His
                485                 490                 495 acg gac cgc agt gac tgg gtc cgc cac ttc ggc gcc gcc gag tgg aat     1536
Thr Asp Arg Ser Asp Trp Val Arg His Phe Gly Ala Ala Glu Trp Asn
            500                 505                 510 cgc ttc gtg gag atg aag aac aag tac gac ccc aag agg ctg ctc tcc    1584
Arg Phe Val Glu Met Lys Asn Lys Tyr Asp Pro Lys Arg Leu Leu Ser
515                 520                 525 ccc ggc cag gac atc ttc aac tga                                     1608
Pro Gly Gln Asp Ile Phe Asn
530                 535

<210> SEQ ID NO 2
<211> LENGTH: 535
<212> TYPE: PRT
<213> ORGANISM: Zea mays

<400> SEQUENCE: 2
```

```
Met Ala Val Val Tyr Tyr Leu Leu Ala Gly Leu Ile Ala Cys Ser
 1               5                  10                  15

His Ala Leu Ala Ala Gly Thr Leu Ala Leu Gly Glu Asp Arg Gly Arg
                 20                  25                  30

Pro Trp Pro Ala Phe Leu Ala Ala Leu Ala Leu Asp Gly Lys Leu Arg
             35                  40                  45

Thr Asp Ser Asn Ala Thr Ala Ala Ser Thr Asp Phe Gly Asn Ile
 50                  55                  60

Thr Ser Ala Leu Pro Ala Ala Val Leu Tyr Pro Ser Ser Thr Gly Asp
 65              70                  75                  80

Leu Val Ala Leu Leu Ser Ala Ala Asn Ser Thr Pro Gly Trp Pro Tyr
                 85                  90                  95

Thr Ile Ala Phe Arg Gly Arg Gly His Ser Leu Met Gly Gln Ala Phe
                100                 105                 110

Ala Pro Gly Gly Val Val Asn Met Ala Ser Leu Gly Asp Ala Ala
             115                 120                 125

Ala Ala Ala Pro Pro Arg Val Asn Val Ser Ala Asp Gly Arg Tyr Val
130                 135                 140

Asp Ala Gly Gly Glu Gln Val Trp Ile Asp Val Leu Arg Ala Ser Leu
145                 150                 155                 160

Ala Arg Gly Val Ala Pro Arg Ser Trp Thr Asp Tyr Leu Tyr Leu Thr
                165                 170                 175

Val Gly Gly Thr Leu Ser Asn Ala Gly Ile Ser Gly Gln Ala Phe Arg
                180                 185                 190

His Gly Pro Gln Ile Ser Asn Val Leu Glu Met Asp Val Ile Thr Gly
                195                 200                 205

His Gly Glu Met Val Thr Cys Ser Lys Gln Leu Asn Ala Asp Leu Phe
                210                 215                 220

Asp Ala Val Leu Gly Gly Leu Gly Gln Phe Gly Val Ile Thr Arg Ala
225                 230                 235                 240

Arg Ile Ala Val Glu Pro Ala Pro Ala Arg Ala Arg Trp Val Arg Leu
                245                 250                 255

Val Tyr Thr Asp Phe Ala Ala Phe Ser Ala Asp Gln Glu Arg Leu Thr
                260                 265                 270

Ala Pro Arg Pro Gly Gly Gly Ala Ser Phe Gly Pro Met Ser Tyr
             275                 280                 285

Val Glu Gly Ser Val Phe Val Asn Gln Ser Leu Ala Thr Asp Leu Ala
             290                 295                 300

Asn Thr Gly Phe Phe Thr Asp Ala Asp Val Ala Arg Ile Val Ala Leu
305                 310                 315                 320

Ala Gly Glu Arg Asn Ala Thr Thr Val Tyr Ser Ile Glu Ala Thr Leu
                325                 330                 335

Asn Tyr Asp Asn Ala Thr Ala Ala Ala Val Asp Gln Glu Leu Ala
                340                 345                 350

Ser Val Leu Gly Thr Leu Ser Tyr Val Glu Gly Phe Ala Phe Gln Arg
                355                 360                 365

Asp Val Ser Tyr Thr Ala Phe Leu Asp Arg Val His Gly Glu Glu Val
             370                 375                 380

Ala Leu Asn Lys Leu Gly Leu Trp Arg Val Pro His Pro Trp Leu Asn
385                 390                 395                 400

Met Phe Val Pro Arg Ser Arg Ile Ala Asp Phe Asp Arg Gly Val Phe
                405                 410                 415
```

```
Lys Gly Ile Leu Gln Gly Thr Asp Ile Val Gly Pro Leu Ile Val Tyr
        420                 425                 430

Pro Leu Asn Lys Ser Met Trp Asp Asp Gly Met Ser Ala Ala Thr Pro
        435                 440                 445

Ser Glu Asp Val Phe Tyr Ala Val Ser Leu Leu Phe Ser Ser Val Ala
        450                 455                 460

Pro Asn Asp Leu Ala Arg Leu Gln Glu Gln Asn Arg Arg Ile Leu Arg
465                 470                 475                 480

Phe Cys Asp Leu Ala Gly Ile Gln Tyr Lys Thr Tyr Leu Ala Arg His
                485                 490                 495

Thr Asp Arg Ser Asp Trp Val Arg His Phe Gly Ala Ala Glu Trp Asn
                500                 505                 510

Arg Phe Val Glu Met Lys Asn Lys Tyr Asp Pro Lys Arg Leu Leu Ser
        515                 520                 525

Pro Gly Gln Asp Ile Phe Asn
    530                 535
```

<210> SEQ ID NO 3
<211> LENGTH: 51
<212> TYPE: DNA
<213> ORGANISM: Artificial Sequence
<220> FEATURE:
<223> OTHER INFORMATION: Synthesized based on sequence from
      Agrobacterium tumefaciens

<400> SEQUENCE: 3
caucaucauc auggatccac caatggatct acgtctaatt ttcggtccaa c          51

<210> SEQ ID NO 4
<211> LENGTH: 42
<212> TYPE: DNA
<213> ORGANISM: Artificial Sequence
<220> FEATURE:
<223> OTHER INFORMATION: Synthesized based on sequence from
      Agrobacterium tumefaciens

<400> SEQUENCE: 4
cuacuacuac uagttaactc acattcgaaa tggtggtcct tc                    42

<210> SEQ ID NO 5
<211> LENGTH: 29
<212> TYPE: DNA
<213> ORGANISM: Zea mays

<400> SEQUENCE: 5
catgccatgg cggtggttta ttacctgct                                   29

<210> SEQ ID NO 6
<211> LENGTH: 31
<212> TYPE: DNA
<213> ORGANISM: Zea mays

<400> SEQUENCE: 6
cgggatcctc atcatcagtt gaagatgtcc t                                31

<210> SEQ ID NO 7
<211> LENGTH: 5622
<212> TYPE: DNA
<213> ORGANISM: Artificial Sequence
<220> FEATURE:
<223> OTHER INFORMATION: Promoter and terminator from Zea mays as found
      in Genbank Accession #S78780; gene from Agrobacterium tumefaciens
      as found in Molecular and General Genetics 216:388-394 (1989).

<400> SEQUENCE: 7

```
gctctagatt atataattta taagctaaac aacccggccc taaagcacta tcgtatcacc      60
tatctaaata agtcacggga gtttcgaacg tccacttcgt cgcacggaat tgcatgtttc     120
ttgttggaag catattcacg caatctccac acataaaggt ttatgtataa acttacattt     180
agctcagttt aattacagtc ttatttggat gcatatgtat ggttctcaat ccatataagt     240
tagagtaaaa aataagttta aattttatct taattcactc caacatatat ggatctacaa     300
tactcatgtg catccaaaca aactacttat attgaggtga atttggtaga aattaaacta     360
acttacacac taagccaatc tttactatat taaagcacca gtttcaacga tcgtcccgcg     420
tcaatattat taaaaaactc ctacatttct ttataatcaa cccgcactct tataatctct     480
tctctactac tataataaga gagtttatgt acaaaataag gtgaaattat ctataagtgt     540
tctggatatt ggttgttggc tcccatattc acacaaccta atcaatagaa aacatatgtt     600
ttattaaaac aaaatttatc atatatcata tatatatata tatcatatat atatataaac     660
cgtagcaatg cacgggcata taactagtgc aacttaatac atgtgtgtat taagatgaat     720
aagagggtat ccaaataaaa aacttgttgc ttacgtatgg atcgaagggg gttggaaacg     780
attaaacgat taaatctctt cctagtcaaa attgaataga aggagattta atatatccca     840
atccccttcg atcatccagg tgcaaccgta taagtcctaa agtggtgagg aacacgaaag     900
aaccatgcat tggcatgtaa agctccaaga atttgttgta tccttaacaa ctcacagaac     960
atcaaccaaa attgcacgtc aagggtattg ggtaagaaac aatcaaacaa atcctctctg    1020
tgtgcaaaga aacacggtga gtcatgccga gatcatactc atctgatata catgcttaca    1080
gctcacaaga cattacaaac aactcatatt gcattacaaa gatcgtttca tgaaaaataa    1140
aataggccgg acaggacaaa aatccttgac gtgtaaagta aatttacaac aaaaaaaaag    1200
ccatatgtca agctaaatct aattcgtttt acgtagatca acaacctgta gaaggcaaca    1260
aaactgagcc acgcagaagt acagaatgat tccagatgaa ccatcgacgt gctacgtaaa    1320
gagagtgacg agtcatatac atttggcaag aaaccatgaa gctgcctaca gccgtatcgg    1380
tggcataaga acacaagaaa ttgtgttaat taatcaaagc tataaataac gctcgcatgc    1440
ctgtgcactt ctccatcacc accactgggt cttcagacca ttagctttat ctactccaga    1500
gcgcagaaga acccgatcga caccatggat ctacgtctaa ttttcggtcc aacttgcaca    1560
ggaaagacat cgactgcgat agctcttgcc cagcagactg gcctcccagt cctctcgctc    1620
gatcgcgtcc aatgctgtcc tcaactatca accggaagcg ggcgaccaac agtggaagaa    1680
ctgaaaggaa cgactcgtct gtaccttgat gatcgccctt tggtaaaggg tatcattaca    1740
gccaagcaag ctcatgaacg gctcattgcg gaggtgcaca atcacgaggc caaaggcggg    1800
cttattcttg agggaggatc tatctcgttg ctcaggtgca tggcgcaaag tcgttattgg    1860
aacgcggatt ttcgttggca tattattcgc aacgagttag cagacgagga gagcttcatg    1920
agcgtggcca agaccagagt taagcagatg ttacgcccct ctgcaggtct ttctattatc    1980
caagagttgg ttcaactttg gagggagcct cggctgaggc ccatactgga agggatcgat    2040
ggatatcgat atgccctgct atttgctacc cagaaccaga tcacgcccga tatgctattg    2100
cagctcgacg cagatatgga gaataaattg attcacggta tcgctcagga gtttctaatc    2160
catgcgcgtc gacaggaaca gaaattccct ttggtgggcg cgacagctgt cgaagcgttt    2220
gaaggaccac catttcgaat gtgagttgat ccccggcggt gtcccccact gaagaaacta    2280
```

```
tgtgctgtag tatagccgct ggctagctag ctagttgagt catttagcgg cgatgattga    2340
gtaataatgt gtcacgcatc accatgcatg ggtggcagtc tcagtgtgag caatgacctg    2400
aatgaacaat tgaaatgaaa agaaaaaagt attgttccaa attaaacgtt ttaaccttt    2460
aataggttta tacaataatt gatatatgtt ttctgtatat gtctaatttg ttatcatcca    2520
tttagatata gacgaaaaaa aatctaagaa ctaaaacaaa tgctaatttg aaatgaaggg    2580
agtatatatt gggataatgt cgatgagatc cctcgtaata tcaccgacat cacacgtgtc    2640
cagttaatgt atcagtgata cgtgtattca catttgttgc gcgtaggcgt acccaacaat    2700
tttgatcgac tatcagaaag tcaacggaag cgagtcgacc tcgagggggg gcccggtacc    2760
aagatatcaa ccgcggaaag atctaagcat gcaagggccc aagtcgacct gcagaagctt    2820
gcatgcctgc agtgcagcgt gacccggtcg tgccctctc tagagataat gagcattgca    2880
tgtctaagtt ataaaaaatt accacatatt tttttgtca cacttgtttg aagtgcagtt    2940
tatctatctt tatacatata tttaaacttt actctacgaa taatataatc tatagtacta    3000
caataatatc agtgttttag agaatcatat aaatgaacag ttagacatgg tctaaaggac    3060
aattgagtat tttgacaaca ggactctaca gtttatctt tttagtgtgc atgtgttctc    3120
cttttttttt gcaaatagct tcacctatat aatacttcat ccatttttatt agtacatcca    3180
tttagggttt agggttaatg gttttttatag actaattttt ttagtacatc tattttattc    3240
tatttagcc tctaaattaa gaaaactaaa actctatttt agtttttta tttaataatt       3300
tagatataaa atagaataaa ataaagtgac taaaaattaa acaaataccc tttaagaaat    3360
taaaaaaact aaggaaacat ttttcttgtt tcgagtagat aatgccagcc tgttaaacgc    3420
cgtcgatcga cgagtctaac ggacaccaac cagcgaacca gcagcgtcgc gtcgggccaa    3480
gcgaagcaga cggcacggca tctctgtcgc tgcctctgga cccctctcga gagttccgct    3540
ccaccgttgg acttgctccg ctgtcggcat ccagaaattg cgtggcggag cggcagacgt    3600
gagccggcac ggcaggcggc ctcctcctcc tctcacggca cggcagctac gggggattcc    3660
tttcccaccg ctccttcgct ttcccttcct cgcccgccgt aataaataga cacccccgcc    3720
acaccctctt tccccaacct cgtgttgttc ggagcgcaca cacacacaac cagatctccc    3780
ccaaatccac ccgtcggcac ctccgcttca aggtacgccg ctcgtcctcc cccccccccc    3840
ctctctacct tctctagatc ggcgttccgg tccatggtta gggcccggta gttctacttc    3900
tgttcatgtt tgtgttagat ccgtgtttgt gttagatccg tgctgctagc gttcgtacac    3960
ggatgcgacc tgtacgtcag acacgttctg attgctaact tgccagtgtt tctctttggg    4020
gaatcctggg atggctctag ccgttccgca gacgggatcg atttcatgat ttttttgtt    4080
tcgttgcata gggtttggtt tgcccttttc ctttatttca atatatgccg tgcacttgtt    4140
tgtcgggtca tcttttcatg ctttttttg tcttggttgt gatgatgtgg tctggttggg    4200
cggtcgttct agatcggagt agaattctgt ttcaaactac ctggtggatt tattaatttt    4260
ggatctgtat gtgtgtgcca tacatattca tagttacgaa ttgaagatga tggatggaaa    4320
tatcgatcta ggataggtat acatgttgat gcgggtttta ctgatgcata tacagagatg    4380
cttttgttc gcttggttgt gatgatgtgg tgtggttggg cggtcgttca ttcgttctag    4440
atcggagtag aatactgttt caaactacct ggtgtattta ttaattttgg aactgtatgt    4500
gtgtgtcata catcttcata gttacgagtt taagatggat ggaaatatcg atctaggata    4560
ggtatacatg ttgatgtggg ttttactgat gcatatacat gatggcatat gcagcatcta    4620
ttcatatgct ctaaccttga gtacctatct attataataa acaagtatgt tttataatta    4680
```

-continued

```
ttttgatctt gatatacttg gatgatggca tatgcagcag ctatatgtgg attttttag      4740 ccctgccttc atacgctatt tatttgcttg gtactgtttc ttttgtcgat gctcaccctg      4800
ttgtttggtg ttacttctgc aggtcgaccg ccggggatcc acacgacacc atgtcccccg      4860
agcgccgccc cgtcgagatc cgcccggcca ccgccgccga catggccgcc gtgtgcgaca      4920
tcgtgaacca ctacatcgag acctccaccg tgaacttccg caccgagccg cagacccccgc    4980 aggagtggat cgacgacctg gagcgcctcc aggaccgcta cccgtggctc gtggccgagg      5040
tggagggcgt ggtggccggc atcgcctacg ccggcccgtg gaaggcccgc aacgcctacg      5100
actggaccgt ggagtccacc gtgtacgtgt cccaccgcca ccagcgcctc ggcctcggct      5160
ccaccctcta cacccacctc ctcaagagca tggaggccca gggcttcaag tccgtggtgg      5220
ccgtgatcgg cctcccgaac gacccgtccg tgcgcctcca cgaggccctc ggctacaccg      5280
cccgcggcac cctccgcgcc gccggctaca agcacggcgg ctggcacgac gtcggcttct      5340
ggcagcgcga cttcgagctg ccggccccgc cgcgcccggt gcgcccggtg acgcagatct      5400
gagtcgacct gcaggcatgc cgctgaaatc accagtctct ctctacaaat ctatctctct      5460
ctataataat gtgtgagtag ttcccagata agggaattag ggttcttata gggtttcgct      5520
catgtgttga gcataataga aaccccttagt atgtatttgt atttgtaaaa tacttctatc     5580
aataaaattt ctaattccta aaaccaaaat ccagtggcga gc                        5622
```

<210> SEQ ID NO 8
<211> LENGTH: 2722
<212> TYPE: DNA
<213> ORGANISM: Artificial Sequence
<220> FEATURE:
<223> OTHER INFORMATION: Promoter from Hordeum vulgare, Plant Journal
6:849-860 (1994); gene from Agrobacterium tumefaciens, Molecular
and General Genetics 216:388-394 (1989); terminator from Zea mays,
Genbank Accession #S78780.

<400> SEQUENCE: 8

```
cggccgctct agaactagtg gatctcgatg tgtagtctac gagaagggtt aaccgtctct      60
tcgtgagaat aaccgtggcc taaaataag ccgatgagga taaataaaat gtggtggtac      120
agtacttcaa gaggtttact catcaagagg atgcttttcc gatgagctct agtagtacat      180
cggacctcac atacctccat tgtggtgaaa tattttgtgc tcatttagtg atgggtaaat      240
tttgtttatg tcactctagg ttttgacatt tcagttttgc cactcttagg ttttgacaaa      300
taatttccat tccgcggcaa aagcaaaaca attttatttt acttttacca ctcttagctt      360
tcacaatgta tcacaaatgc cactctagaa attctgttta tgccacagaa tgtgaaaaaa      420
aacactcact tatttgaagc caaggtgttc atggcatgga aatgtgacat aaagtaacgt      480
tcgtgtataa gaaaaaattg tactcctcgt aacaagagac ggaaacatca tgagacaatc      540
gcgtttggaa ggctttgcat caccttggga tgatgcgcat gaatggagtc gtctgcttgc      600
tagccttcgc ctaccgccca ctgagtccgg gcggcaacta ccatcggcga acgacccagc      660
tgacctctac cgaccggact tgaatgcgct accttcgtca gcgacgatgg ccgcgtacgc      720
tggcgacgtg cccccgcatg catggcggca catggcgagc tcagaccgtg cgtggctggc      780
tacaaatacg taccccgtga gtgccctagc tagaaactta cacctgcaac tgcgagagcg      840
agcgtgtgag tgtagccgag tagatccccc gggctgcagc ttattttac aacaattacc      900 aacaacaaca aacaacaaac aacattacaa ttactattta caattacagt cgacggatca      960
agtgcaaagg tccgccttgt ttctcctctg tctcttgatc tgactaatct tggtttatga      1020
```

-continued

```
ttcgttgagt aattttgggg aaagcttcgt ccacagtttt tttttcgatg aacagtgccg    1080
cagtggcgct gatcttgtat gctatcctgc aatcgtggtg aacttatgtc ttttatatcc    1140
ttcactacca tgaaaagact agtaatcttt ctcgatgtaa catcgtccag cactgctatt    1200
accgtgtggt ccatccgaca gtctggctga acacatcata cgatattgag caaagatcga    1260
tctatcttcc ctgttcttta atgaaagacg tcattttcat cagtatgatc taagaatgtt    1320
gcaacttgca aggaggcgtt tctttctttg aatttaacta actcgttgag tggccctgtt    1380
tctcggacgt aaggcctttg ctgctccaca catgtccatt cgaattttac cgtgtttagc    1440
aagggcgaaa agtttgcatc ttgatgattt agcttgacta tgcgattgct ttcctggacc    1500
cgtgcagctg cggacggatc caccatggat ctacgtctaa ttttcggtcc aacttgcaca    1560
ggaaagacat cgactgcgat agctcttgcc cagcagactg gcctcccagt cctctcgctc    1620
gatcgcgtcc aatgctgtcc tcaactatca accggaagcg ggcgaccaac agtggaagaa    1680
ctgaaaggaa cgactcgtct gtaccttgat gatcgcccct tggtaaaggg tatcattaca    1740
gccaagcaag ctcatgaacg gctcattgcg gaggtgcaca atcacgaggc caaaggcggg    1800
cttattcttg agggaggatc tatctcgttg ctcaggtgca tggcgcaaag tcgttattgg    1860
aacgcggatt ttcgttggca tattattcgc aacgagttag cagacgagga gagcttcatg    1920
agcgtggcca agaccagagt taagcagatg ttacgcccct ctgcaggtct ttctattatc    1980
caagagttgg ttcaactttg gagggagcct cggctgaggc ccatactgga agggatcgat    2040
ggatatcgat atgccctgct atttgctacc cagaaccaga tcacgcccga tatgctattg    2100
cagctcgacg cagatatgga gaataaattg attcacggta tcgctcagga gtttctaatc    2160
catgcgcgtc gacaggaaca gaaattccct ttggtgggcg cgacagctgt cgaagcgttt    2220
gaaggaccac catttcgaat gtgagttgat ccccggcggt gtcccccact gaagaaacta    2280
tgtgctgtag tatagccgct ggctagctag ctagttgagt catttagcgg cgatgattga    2340
gtaataatgt gtcacgcatc accatgcatg ggtggcagtc tcagtgtgag caatgacctg    2400
aatgaacaat tgaaatgaaa agaaaaaagt attgttccaa attaaacgtt ttaaccttt     2460 aataggttta tacaataatt gatatatgtt ttctgtatat gtctaatttg ttatcatcca    2520
tttagatata gacgaaaaaa aatctaagaa ctaaaacaaa tgctaatttg aaatgaaggg    2580
agtatatatt gggataatgt cgatgagatc cctcgtaata tcaccgacat cacacgtgtc    2640 cagtaatgt atcagtgata cgtgtattca catttgttgc gcgtaggcgt acccaacaat     2700
tttgatcgac tatcagaaag tc                                             2722
```

<210> SEQ ID NO 9
<211> LENGTH: 2722
<212> TYPE: DNA
<213> ORGANISM: Artificial Sequence
<220> FEATURE:
<223> OTHER INFORMATION: Promoter from Zea mays, U.S. patent application
      09/377,648; gene from Agrobacterium tumefaciens, Molecular and
      General Genetics 216:388-394 (1989); terminator from Solanum
      tuberosum, Plant Cell 1(1):115-122 (1989).

<400> SEQUENCE: 9

```
cggccgctct agaactagtg gatctcgatg tgtagtctac gagaagggtt aaccgtctct      60
tcgtgagaat aaccgtggcc taaaaataag ccgatgagga taaataaaat gtggtggtac     120
agtacttcaa gaggtttact catcaagagg atgcttttcc gatgagctct agtagtacat     180
cggacctcac ataccttccat tgtggtgaaa tattttgtgc tcatttagtg atgggtaaat    240
```

-continued

```
tttgtttatg tcactctagg ttttgacatt tcagttttgc cactcttagg ttttgacaaa      300
taatttccat tccgcggcaa agcaaaaca attttatttt acttttacca ctcttagctt       360
tcacaatgta tcacaaatgc cactctagaa attctgttta tgccacagaa tgtgaaaaaa      420
aacactcact tatttgaagc caaggtgttc atggcatgga aatgtgacat aaagtaacgt      480
tcgtgtataa gaaaaaattg tactcctcgt aacaagagac ggaaacatca tgagacaatc      540
gcgtttggaa ggctttgcat caccttttgga tgatgcgcat gaatggagtc gtctgcttgc    600
tagccttcgc ctaccgccca ctgagtccgg gcggcaacta ccatcggcga acgacccagc     660
tgacctctac cgaccggact tgaatgcgct accttcgtca gcgacgatgg ccgcgtacgc     720
tggcgacgtg cccccgcatg catggcggca catggcgagc tcagaccgtg cgtggctggc    780
tacaaatacg taccccgtga gtgccctagc tagaaactta cacctgcaac tgcgagagcg     840
agcgtgtgag tgtagccgag tagatccccc gggctgcagc ttattttttac aacaattacc    900
aacaacaaca aacaacaaac aacattacaa ttactatttta caattacagt cgacggatca    960
agtgcaaagg tccgccttgt ttctcctctg tctcttgatc tgactaatct tggtttatga    1020
ttcgttgagt aattttgggg aaagcttcgt ccacagtttt tttttcgatg aacagtgccg    1080
cagtggcgct gatcttgtat gctatcctgc aatcgtggtg aacttatgtc ttttatatcc    1140
ttcactacca tgaaaagact agtaatcttt ctcgatgtaa catcgtccag cactgctatt    1200
accgtgtggt ccatccgaca gtctggctga acacatcata cgatattgag caaagatcga    1260
tctatcttcc ctgttcttta atgaaagacg tcattttcat cagtatgatc taagaatgtt    1320
gcaacttgca aggaggcgtt tcttttctttg aatttaacta actcgttgag tggccctgtt   1380
tctcggacgt aaggcctttg ctgctccaca catgtccatt cgaattttac cgtgtttagc    1440
aagggcgaaa agtttgcatc ttgatgattt agcttgacta tgcgattgct ttcctggacc    1500
cgtgcagctg cggacggatc caccatggat ctacgtctaa ttttcggtcc aacttgcaca    1560
ggaaagacat cgactgcgat agctcttgcc cagcagactg gcctcccagt cctctcgctc    1620
gatcgcgtcc aatgctgtcc tcaactatca accggaagcg ggcgaccaac agtggaagaa    1680
ctgaaaggaa cgactcgtct gtaccttgat gatcgccctt tggtaaaggg tatcattaca    1740
gccaagcaag ctcatgaacg gctcattgcg gaggtgcaca atcacgaggc caaaggcggg    1800
cttattcttg agggaggatc tatctcgttg ctcaggtgca tggcgcaaag tcgttattgg    1860
aacgcggatt tcgttggca tattattcgc aacgagttag cagacgagga gagcttcatg     1920
agcgtggcca agaccagagt taagcagatg ttacgcccct ctgcaggtct ttctattatc    1980
caagagttgg ttcaactttg gagggagcct cggctgaggc ccatactgga agggatcgat    2040
ggatatcgat atgccctgct atttgctacc cagaaccaga tcacgcccga tatgctattg    2100
cagctcgacg cagatatgga gaataaattg attcacggta tcgctcagga gtttctaatc    2160
catgcgcgtc gacaggaaca gaaattccct ttggtgggcg cgacagctgt cgaagcgttt    2220
gaaggaccac catttcgaat gtgagttgat ccccggcggt gtcccccact gaagaaacta    2280
tgtgctgtag tatagccgct ggctagctag ctagttgagt catttagcgg cgatgattga    2340
gtaataatgt gtcacgcatc accatgcatg ggtggcagtc tcagtgtgag caatgacctg    2400
aatgaacaat tgaaatgaaa agaaaaagt attgttccaa attaaacgtt ttaacctttt      2460
aataggttta tacaataatt gatatatgtt ttctgtatat gtctaatttg ttatcatcca    2520
tttagatata gacgaaaaaa aatctaagaa ctaaaacaaa tgctaatttg aaatgaaggg    2580
```

```
agtatatatt gggataatgt cgatgagatc cctcgtaata tcaccgacat cacacgtgtc    2640
cagttaatgt atcagtgata cgtgtattca catttgttgc gcgtaggcgt acccaacaat    2700
tttgatcgac tatcagaaag tc                                             2722
```

<210> SEQ ID NO 10
<211> LENGTH: 23
<212> TYPE: DNA
<213> ORGANISM: Artificial Sequence
<220> FEATURE:
<223> OTHER INFORMATION: Synthesized based on sequence from
      Agrobacterium tumefaciens

<400> SEQUENCE: 10

```
gcgtccaatg ctgtcctcaa cta                                              23
```

<210> SEQ ID NO 11
<211> LENGTH: 23
<212> TYPE: DNA
<213> ORGANISM: Artificial Sequence
<220> FEATURE:
<223> OTHER INFORMATION: Synthesized based on sequence from
      Agrobacterium tumefaciens

<400> SEQUENCE: 11

```
gctctcctcg tctgctaact cgt                                              23
```

<210> SEQ ID NO 12
<211> LENGTH: 3017
<212> TYPE: DNA
<213> ORGANISM: Artificial Sequence
<220> FEATURE:
<223> OTHER INFORMATION: Promoter from Zea mays, Genbank Accession
      #L22344; Gene from Agrobacterium tumefaciens, Molecular and
      General Genetics 216:388-394 (1989); terminator from Zea mays,
      Genbank Accession #L22345.

<400> SEQUENCE: 12

```
ttgccgagtg ccatccttgg acactcgata agtatatttt tattttttt attttgccaa      60 ccaaactttt tgtggtatgt tcctacacta tgtagatcta catgtaccat tttggcacaa    120
ttacatattt acaaaaatgt tttctataaa tattagattt agttcgttta tttgaatttc    180
ttcggaaaat tcacatttaa actgcaagtc actcgaaaca tggaaaaccg tgcatgcaaa    240
ataaatgata tgcatgttat ctagcacaag ttacgaccga tttcagaagc agaccagaat    300
cttcaagcac catgctcact aaacatgacc gtgaacttgt tatctagttg tttaaaaatt    360
gtataaaaca caaataaagt cagaaattaa tgaaacttgt ccacatgtca tgatatcata    420
tatagaggtt gtgataaaaa tttgataatg tttcggtaaa gttgtgacgt actatgtgta    480
gaaacctaag tgacctacac ataaaatcat agagtttcaa tgtagttcac tcgacaaaga    540
ctttgtcaag tgtccgataa aaagtactcg acaaagaagc cgttgtcgat gtactgttcg    600
tcgagatctc tttgtcgagt gtcacactag gcaaagtctt tacggagtgt ttttcaggct    660
ttgacactcg gcaaagcgct cgattccagt agtgacagta atttgcatca aaaatagctg    720
agagatttag gccccgtttc aatctcacgg gataaagttt agcttcctgc taaactttag    780
ctatatgaat tgaagtgcta agttttagtt tcaattacca ccattagctc tcctgtttag    840
attacaaatg gctaaaagta gctaaaaaat agctgctaaa gtttatctcg cgagattgaa    900
acagggcctt aaaatgagtc aactaataga ccaactaatt attagctatt agtcgttagc    960
ttctttaatc taagctaaaa ccaactaata gcttatttgt tgaattacaa ttagctcaac   1020
```

-continued

```
ggaattctct gtttttctaa aaaaaaactg ccCctctctt acagcaaatt gtccgctgcc    1080
cgtcgtccag atacaatgaa cgtacctagt aggaactctt ttacacgctc ggtcgctcgc    1140
cgcggatcgg agtccccgga acacgacacc actgtggaac acgacaaagt ctgctcagag    1200
gcggccacac cctggcgtgc accgagccgg agcccggata agcacggtaa ggagagtacg    1260
gcgggacgtg gcgacccgtg tgtctgctgc cacgcagcct tcctccacgt agccgcgcgg    1320
ccgcgccacg taccagggcc cggcgctggt ataaatgcgc gccacctccg ctttagttct    1380
gcatacagcc aacccaagga tccaacaatg gatctacgtc taatttttcgg tccaacttgc   1440
acaggaaaga catcgactgc gatagctctt gcccagcaga ctggcctccc agtcctctcg    1500
ctcgatcgcg tccaatgctg tcctcaacta tcaaccggaa gcgggcgacc aacagtggaa    1560
gaactgaaag gaacgactcg tctgtacctt gatgatcgcc ctttggtaaa gggtatcatt    1620
acagccaagc aagctcatga acggctcatt gcggaggtgc acaatcacga ggccaaaggc    1680
gggcttattc ttgagggagg atctatctcg ttgctcaggt gcatggcgca aagtcgttat    1740
tggaacgcgg attttcgttg gcatattatt cgcaacgagt tagcagacga ggagagcttc    1800
atgagcgtgg ccaagaccag agttaagcag atgttacgcc cctctgcagg tctttctatt    1860
atccaagagt tggttcaact ttggagggag cctcggctga ggcccatact ggaagggatc    1920
gatggatatc gatatgccct gctatttgct acccagaacc agatcacgcc cgatatgcta    1980
ttgcagctcg acgcagatat ggagaataaa ttgattcacg gtatcgctca ggagtttcta    2040
atccatgcgc gtcgacagga acagaaattc cctttggtgg gcgcgacagc tgtcgaagcg    2100
tttgaaggac caccatttcg aatgtgagtt aactatgtac gtaagcggca ggcagtgcaa    2160
taagtgtggc tctgtagtat gtacgtgcgg gtacgatgct gtaagctact gaggcaagtc    2220
cataaataaa taatgacacg tgcgtgttct ataatctctt cgcttcttca tttgtcccct    2280
tgcggagttt ggcatccatt gatgccgtta cgctgagaac agacacagca gacgaaccaa    2340
aagtgagttc ttgtatgaaa ctatgaccct tcatcgctag gctcaaacag caccccgtac    2400
gaacacagca aattagtcat ctaactatta gcccctacat gtttcagacg atacataaat    2460
atagcccatc cttagcaatt agctattggc cctgcccatc ccaagcaatg atctcgaagt    2520
attttttaata tatagtattt ttaatatgta gcttttaaaa ttagaagata attttgagac    2580
aaaaatctcc aagtattttt ttgggtattt tttactgcct ccgttttttct ttatttctcg    2640
tcacctagtt taattttgtg ctaatcggct ataaacgaaa cagagagaaa agttactcta    2700
aaagcaactc caacagatta gatataaatc ttatatcctg cctagagctg ttaaaaagat    2760
agacaacttt agtggattag tgtatgcaac aaactctcca aatttaagta tcccaactac    2820
ccaacgcata tcgttcccctt ttcattggcg cacgaacttt cacctgctat agccgacgta    2880
catgttcgtt ttttttgggc ggcgcttact ttcttccccg ttcgttctca gcatcgcaac    2940
tcaatttgtt atggcggaga agcccttgta tcccaggtag taatgcacag atatgcatta    3000
ttattattca taaaaga                                                    3017
```

REGULATED EXPRESSION OF GENES IN PLANT SEEDS

CROSS REFERENCE TO RELATED APPLICATION

This application claims the benefit of Application 60/129,844 filed Apr. 16, 1999.

FIELD OF THE INVENTION

This invention relates generally to the field of plant molecular biology. More specifically, this invention relates to methods and reagents for the temporal and/or spatial expression of genes that affect metabolically effective levels of cytokinins in plant seeds, as well as in the maternal tissue from which such seeds arise, including developing ears, female inflorescences, ovaries, female florets, aleurone, pedicel, and pedicel-forming regions.

BACKGROUND OF THE INVENTION

Cytokinins have been demonstrated to play a fundamental role in establishing seed size, decreasing tip kernel abortion and increasing seed set during unfavorable environmental conditions. The first naturally occurring cytokinin was purified in 1963 (Letham, D. S., *Life Sci.* 8:569–573 (1963)) from immature kernels of *Zea mays* and identified as 6-(4-hydroxy-3-methylbut-trans-2-enylamino) purine, more commonly known today as zeatin. In the main all naturally occurring cytokinins appear to be purine derivatives with a branched 5-carbon $N^6$ substitutent. (See: McGaw, B. A., In: Plant Hormones and their Role in Plant Growth and Development, ed. P. J. Davies, Martinus Nijhoff Publ., Boston, 1987, Chap B3, Pgs. 76–93, the contents of which are incorporated by reference for purposes of background.) While some 25 different naturally occurring cytokinins have been identified, those regarded as particularly active are $N^6$ ($\Delta^2$-isopentenyl) adenosine (iP), zeatin (Z), diHZ, benzyladenine (BAP) and their 9-ribosyl (and in the case of Z and diHZ, their O-glucosyl) derivatives. However, such activity is markedly reduced in the 7- and 9-glucosyl and 9-alanyl conjugates. These latter compounds may be reflective of deactivation or control mechanisms.

The metabolism of cytokinins in plants is complex. Multi-step biochemical pathways are known for the biosynthesis and degradation of cytokinins. At least two major routes of cytokinin biosynthesis are recognized. The first involves transfer RNA (tRNA) as an intermediate. The second involves de novo (direct) biosynthesis. In the first case, tRNAs are known to contain a variety of hypermodified bases (among them are certain cytokinins). These modifications are known to occur at the tRNA polymer level as a post-transcriptional modification. The branched 5-carbon $N^6$ substituent is derived from mevalonic acid pyrophosphate, which undergoes decarboxylation, dehydration, and isomerization to yield $\Delta^2$-isopentenyl pyrophosphate (iPP). The latter condenses with the relevant adenosine residue in the tRNA. Further modifications are then possible. Ultimately the tRNAs are hydrolyzed to their component bases, thereby forming a pool of available free cytokinins.

Alternately, enzymes have been discovered that catalyze the formation of cytokinins de novo, i.e., without a tRNA intermediate. The ipt gene utilized in the practice of this invention is one such gene. The formation of free cytokinins is presumed to begin with [9R5'P] iP. This compound is rapidly and stereospecifically hydroxylated to give the zeatin derivatives from which any number of further metabolic events may ensue. Such events include but are not limited to (1) conjugation, incorporating ribosides, ribotides, glucosides, and amino acids; (2) hydrolysis; (3) reduction; and (4) oxidation. While each enzyme in these pathways is a candidate as an effector of cytokinin levels, enzymes associated with rate-limiting steps have particular utility in the practice of this invention.

One such enzyme is isopentenyl transferase (ipt). An isolated gene encoding ipt was described by van Larebeke et al., (*Nature* 252:169–170(1974)). Smigocki et al. (*Proc. Nat'l. Acad. Sci.* (*USA*) 85:5131–5135(1988)), employing the ipt gene from *A. tumefaciens* operably linked to either the 35S or NOS promoter, showed a generalized effect on shoot organogenesis and zeatin levels. Such unregulated production of cytokinins can result in unwanted pleiotropic effects. For example, with the constructions identified above, Smigocki et al. (supra) reported that typically complete inhibition of root formation was observed.

Attempts followed to express the ipt gene in a more controlled fashion. Medford et al. (*The Plant Cell* 1:403–413 (1989)) reported placing the ipt gene under the control of a heat-inducible promoter and expressing same in transgenic rooted tobacco plants. While the levels of cytokinin rose dramatically following heat treatment, the promoters were not wholly satisfactory because the plants exhibited phenotypes associated with excess cytokinin levels even in the absence of thermal induction. See also: Schumulling, T. et al. (*FEBS Letters* 249(2):401–406(1989)). A more regulated response was reported in PCT Patent Application Publication No. WO91/01323, 7 Feb. 1991, and PCT Patent Application Publication No. WO93/07272, 15 Apr. 1993, both assigned on their face to Calgene, in which the ipt gene was fused to the chalcone synthase (chs) promoter from *Antirrhinum majus* and expressed in potato.

Additional ipt gene/promoter constructions have been reported. Smigocki et al., in U.S. Pat. No. 5,496,732, disclosed a gene construct capable of conferring enhanced insect resistance comprising a wound-inducible promoter fused to an ipt gene. Houck et al., in U.S. Pat. Nos. 4,943,674 and 5,177,307, disclosed several promoters (2AII, Z130 and Z70) coupled with genes encoding enzymes in the cytokinin metabolic pathway, in particular ipt for expression of such enzymes in tomato fruit. Amasino et al., in PCT Patent Application Publication WO96/29858 disclosed two senescence gene promoters operably linked to an ipt gene to inhibit leaf senescence in tobacco. See also: Gan, S. et al., (*Science* 270:1986–1988 (1995)). Roeckel, P. et al., (*Transgenic Res.* 6(2):133–141 (1997)) transformed canola and tobacco with an ipt gene under the control of a 2S albumin promoter from *Agrobacterium*. Increase in branching of inflorescences was noted, but increases in seed yield and seed weight were not observed.

There still exists a need for the controlled expression, both temporally and spatially, of cytokinin metabolic genes in plant seed and in those maternal tissues in which seed development takes place. This invention addresses this need by providing several useful genetic constructs and methods to modulate effective levels of cytokinin in plant seeds, developing plant seeds, and related maternal tissues. These related maternal tissues would include such tissues as the female floret, the ovary, aleurone, pedicel, and the pedicel-forming region. The maternal tissues are also referred to as "grain initials" or "seed initials".

This invention differs from the foregoing approaches in that it provides tools and reagents that allow the skilled artisan, by the application of, inter alia, transgenic methodologies to influence the metabolic flux in respect to the cytokinin metabolic pathway in seed. This influence may be either anabolic or catabolic, by which is meant the influence may act to increase the flow resulting from the biosynthesis of cytokinin and/or decrease the degradation (i.e., catabolism of cytokinins). A combination of both approaches is also contemplated by this invention.

SUMMARY OF THE INVENTION

It is therefore an object of the present invention to provide plants, particularly transgenic corn, which have enhanced levels of cytokinins in the seed without corresponding detrimental effects.

It is a further object of the present invention to provide transgenic plant lines with dominant, heritable phenotypes which are useful in breeding programs designed to produce commercial products with improved seed size, decreased tip kernel abortion and increased seed set during unfavorable environmental conditions.

In accordance with this aspect of the invention there are provided isolated nucleic acid molecules encoding cytokinin metabolic enzymes, mRNAs, cDNAs, genomic DNAs and, in further embodiments of this aspect of the invention, biologically useful variants, analogs or derivatives thereof, or fragments thereof, including fragments of the variants, analogs and derivatives.

Other embodiments of the invention are naturally occurring allelic variants of the nucleic acid molecules in the sequences provided which encode cytokinin metabolic enzymes.

In accordance with another aspect of the invention there are provided polypeptides which comprise cytokinin metabolic enzymes as well as biologically or diagnostically useful fragments thereof, as well as variants, derivatives and analogs of the foregoing and fragments thereof.

It also is an object of the invention to provide cytokinin metabolic polypeptides, particularly ipt and cytokinin oxidase, that may be employed for modulation of cytokinin levels in seed.

In a preferred embodiment of this aspect of the invention there are provided methods for producing the polypeptides, comprising culturing host cells having expressibly incorporated therein a polynucleotide under conditions for the temporal and/or spatial expression of cytokinin metabolic enzymes in seed, and then optionally recovering the expressed polypeptide.

In accordance with another object of the invention there are provided products, compositions, processes and methods that utilize the aforementioned polypeptides and polynucleotides for research, biological and agricultural purposes.

In accordance with yet another aspect of the present invention, there are provided inhibitors to such polypeptides, useful for modulating the activity and/or expression of the polypeptides. In particular, there are provided antibodies against such polypeptides.

In accordance with certain embodiments of the invention there are probes that hybridize to cytokinin metabolic enzyme polynucleotide sequences useful as molecular markers in breeding programs.

In certain additional preferred embodiments of this aspect of the invention there are provided antibodies against the cytokinin catabolic enzymes. In certain particularly preferred embodiments in this regard, the antibodies are selective for the entire class of the cytokinin catabolic enzymes, irrespective of species of origin, as well as species-specific antibodies.

In accordance with yet another aspect of the present invention, there are provided cytokinin enzyme agonists and antagonists. Among preferred antagonists are those which bind to cytokinin catabolic enzymes (e.g., to cytokinin oxidase) so as to inhibit the binding of binding molecules; or to destabilize the complex formed between the cytokinin catabolic enzyme and the binding molecule, to prevent further biological activity arising from the cytokinin catabolic enzyme. Among preferred agonists are molecules that bind to or interact with cytokinin biosynthetic enzymes so as to stimulate one or more effects of a particular cytokinin biosynthetic enzyme or which enhance expression of the enzyme and which also preferably result in a modulation of cytokinin accumulation.

It is therefore an object of the present invention to provide plants, particularly transgenic corn, which have enhanced levels of cytokinins in the seed, the developing seed, and the maternal tissues associated with seed development. These levels act as a metabolic buffer to ameliorate the effects of transient stresses, particularly during the lag phase of seed development, to thus improve corn stress tolerance and yield stability.

It is a further object of the present invention to provide transgenic corn which has enhanced levels of cytokinins in the seed to provide commercial products with improved seed size, decreased tip kernel abortion and increased seed set during unfavorable environmental conditions.

It is a further object of this invention to provide a method for producing fertile, transgenic plants capable of the regulated expression of a cytokinin modulating gene in developing seeds, comprising introducing into plant host cells a genetic construct capable of preferential temporal and/or spatial expression of a cytokinin-modulating gene in developing seed and the maternal tissues associated with seed development, under conditions sufficient for the stable integration of the construct into the genome of said cells, and regenerating and recovering said fertile transgenic plants.

It is a further object of this invention to provide a fertile transgenic plant comprising a genetic construct stably integrated into the genome thereof, said construct capable of the temporal and/or spatial modulation of cytokinin levels in developing seed of said plant.

It is a further object of this invention to provide an isolated recombinant DNA comprising a genetic construct that comprises a promoter directing temporal and/or spatial gene expression in plant seed operatively linked to a cytokinin modulating gene.

It is a further object of this invention to provide a method for improving stress tolerance and yield stability in plants in need thereof, comprising stably introducing into cells of said plants a genetic construct capable of preferentially expressing cytokinin modulating genes during the lag phase of plant seed development, and regenerating and recovering plants from said cells.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

FIG. 1A—Embryo: This Figure shows that embryo-preferred overexpression of ipt increases embryo cytokinin levels, particularly ZR and Z9G (range of 2 to 8-fold difference). In contrast, Z levels are unchanged and IPAR is not detectable at either developmental stage. Abbreviations: Z=zeatin, ZR (or [9R]Z)=zeatin riboside, Z9G (or [9G]Z) =zeatin-9-glucoside, IPA or [9R]iP=isopentenyladenosine, IPAR (or [9R-5'P]iP)=isopentenyladenosine-5'-monophosphate, and DAP=Days After Pollination.

FIG. 1B—Endosperm: This Figure shows that embryo-preferred ipt overexpression altered endosperm cytokinin levels but less than those in the embryo (range of only 10 to 30% difference). Abbreviations used as in FIG. 1A.

GLOSSARY

The following illustrative explanations are provided to facilitate understanding of certain terms used frequently herein, particularly in the Examples. The explanations are provided as a convenience and are not limitative of the invention.

CYTOKININ METABOLIC ENZYME-BINDING MOLECULE, as used herein, refers to molecules or ions which bind or interact specifically with cytokinin metabolic enzyme polypeptides or polynucleotides of the present invention, including, for example enzyme substrates, cell membrane components and classical receptors. Binding between polypeptides of the invention and such molecules, including binding or interaction molecules, may be exclusive to polypeptides of the invention, which is preferred, or it may be highly specific for polypeptides of the invention, which is also preferred, or it may be highly specific to a group of proteins that includes polypeptides of the invention, which is preferred, or it may be specific to several groups of proteins at least one of which includes a polypeptide of the invention. Binding molecules also include antibodies and antibody-derived reagents that bind specifically to polypeptides of the invention.

CYTOKININ RESPONSIVE COMPONENT, as used herein, generally means a cellular constituent that binds to or otherwise interacts with a cytokinin resulting in the transmission of an intra- or inter-cellular signal and eliciting one or more cellular responses to the presence or absence or fluctuation in the levels of cytokinins.

DEVELOPING PLANT SEEDS, as used herein, generally means the maternal plant tissues which after pollination are capable of giving rise to a plant seed. This maternal plant tissue includes such tissue as female florets, ovaries, aleurone, pedicel, and pedicel-forming region.

GENETIC ELEMENT, as used herein, generally means a polynucleotide comprising a region that encodes a polypeptide or a polynucleotide region that regulates replication, transcription or translation or other processes important to expression of the polypeptide in a host cell, or a polynucleotide comprising both a region that encodes a polypeptide and a region operably linked thereto that regulates expression. Genetic elements may be comprised within a vector that replicates as an episomal element; that is, as a molecule physically independent of the host cell genome. They may be comprised within plasmids. Genetic elements also may be comprised within a host cell genome; not in their natural state but, rather, following manipulation such as isolation, cloning and introduction into a host cell in the form of purified DNA or in a vector, among others.

GERMPLASM, as used herein, means a set of genetic entities, which may be used in a conventional breeding program to develop new plant varieties.

HIGH CYTOKININ TRANSGENIC, as used herein, means an entity, which, as a result of recombinant genetic manipulation, produces seed with a heritable increase in cytokinin and/or decrease in auxin.

HOST CELL, as used herein, is a cell which has been transformed or transfected, or is capable of transformation or transfection by an exogenous polynucleotide sequence. Exogenous polynucleotide sequence is defined to mean a sequence not naturally in the cell. This includes transformation to incorporate additional copies of an endogenous polynucleotide.

IDENTITY and SIMILARITY, as used herein, and as known in the art, are relationships between two polypeptide sequences or two polynucleotide sequences, as determined by comparing the sequences. In the art, identity also means the degree of sequence relatedness between two polypeptide or two polynucleotide sequences as determined by the match between two strings of such sequences. Both identity and similarity can be readily calculated (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). Methods commonly employed to determine identity or similarity between two sequences include, but are not limited to those disclosed in Carillo, H., and Lipman, D., SIAM *J. Applied Math.*, 48:1073 (1988). Preferred methods to determine identity are designed to give the largest match between the two sequences tested. Methods to determine identity and similarity are codified in computer programs. Typical computer program methods to determine identity and similarity between two sequences include: GCG program package (Devereux, J., et al., *Nucleic Acids Research* 12(1):387 (1984)), BLASTP, BLASTN, FASTA and TFASTA (Atschul, S. F. et al., *J. Mol. Biol.* 215:403 (1990)).

For purposes of defining the present invention, the Gap program is used. The algorithm used for the Gap program is that of Needleman and Wunsch (*J. Mol. Biol.* 48:443–453 [1970]). The parameters used are as follows: for nucleotide comparisons the gap creation penalty=50, gap extension penalty=3; for amino acid comparisons the gap creation penalty=12, the gap extension penalty=4.

ISOLATED, as used herein, means altered "by the hand of man" from its natural state; i.e., that, if it occurs in nature, it has been changed or removed from its original environment, or both. For example, a naturally occurring polynucleotide or a polypeptide naturally present in a living organism in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs. As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

LIGATION, as used herein, refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., *MOLECULAR CLONING, A LABORATORY MANUAL*, 2nd Ed.; Cold Spring Harbor Laboratory Press, Cold Spring Harbor, N.Y. (1989) and Maniatis et al., pg. 146, as cited below.

OLIGONUCLEOTIDE(S), as used herein, refers to short polynucleotides. Often the term refers to single-stranded deoxyribonucleotides, but it can refer as well to single- or double-stranded ribonucleotides, RNA:DNA hybrids and double-stranded DNAs, among others. Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA- mediated techniques and by expression of DNAs in cells and organisms. Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP. The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

OPERABLY LINKED, as used herein, includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

PLANT, as used herein, includes reference to whole plants, plant parts or organs (e.g., leaves, stems, roots, etc.), plant cells, seeds and progeny of same. Plant cell, as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants. A particularly preferred plant is *Zea mays*.

PLASMIDS, as used herein, generally are designated herein by a lower case p preceded and/or followed by capital letters and/or numbers, in accordance with standard naming conventions that are familiar to those of skill in the art. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent from the present disclosure to those of skill.

POLYNUCLEOTIDE(S), as used herein, generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single- and double-stranded regions or single-, double- and triple-stranded regions, single- and double-stranded RNA, and RNA that is a mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically-, enzymatically- or metabolically-modified forms of polynucleotides, as well as the chemical forms of DNA and RNA characteristic of viruses and cells, including inter alia, simple and complex cells.

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance *PROTEINS—STRUCTURE AND MOLECULAR PROPERTIES,* 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York (1983); Seifter et al., *Meth. Enzymol.* 182:626–646 (1990) and Rattan et al., *Protein Synthesis: Posttranslational Modifications and Aging, Ann. N.Y. Acad. Sci.* 663:48–62 (1992). It will be appreciated, as is well known and as noted above, that polypeptides are not always entirely linear. For instance, polypeptides may be branched as a result of ubiquitination, and they may be circular, with or without branching, generally as a result of posttranslation events, including natural processing events and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the $NH_2$-terminus may be deleted. Accordingly, this invention contemplates the use of both the methionine-containing and the methionine-less amino terminal variants of the protein of the invention. The modifications that occur in a polypeptide often will be a function of how it is made. For polypeptides made by expressing a cloned gene in a host, for instance, the nature and extent of the modifications in large part will be determined by the host cell post-translational modification capacity and the modification signals present in the polypeptide amino acid sequence. For instance, as is well known, glycosylation often does not occur in bacterial hosts such as, for example, *E. coli.* Accordingly, when glycosylation is desired, a polypeptide should be expressed in a glycosylating host, generally an eukaryotic cell. Similar considerations apply to other modifications. It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesized by expressing a polynucleotide in a host cell.

PROMOTER, as used herein, includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells, such as *Agrobacterium* or *Rhizobium*. Examples of promoters under developmental control include promoters that preferentially initiate transcription in certain tissues, such as leaves, roots, or seeds or spatially in regions such as endosperm or embryos. Such promoters are referred to as "tissue preferred". Promoters that initiate transcription only in certain tissue are referred to as "tissue specific". A temporally regulated promoter drives expression at particular times, such as between 0–25 days after pollination. A "cell type" specific promoter primarily drives expression in certain cell types in one or more organs, for example, vascular cells in roots or leaves. An "inducible" promoter is a promoter which is under environmental control and may be inducible or derepressible. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

RELATED MATERNAL TISSUE, as used herein, includes maternal plant tissues, such as female florets, ovaries, aleurone, pedicel, and pedicel-forming region, either pre-pollination or upon pollination. Pre-pollination seed tissues can also be referred to as "grain initials" or "seed initials".

TRANSFORMATION, as used herein, is the process by which a cell is "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to higher eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cells containing the exogenous DNA.

VARIANT(S), as used herein, of polynucleotides or polypeptides, as the term is used herein, are polynucleotides or polypeptides that differ from a reference polynucleotide or polypeptide, respectively. Variants in this sense are described below and elsewhere in the present disclosure in greater detail. With reference to polynucleotides, generally, differences are limited such that the nucleotide sequences of the reference and the variant are closely similar overall and, in many regions, identical. As noted below, changes in the nucleotide sequence of the variant may be silent. That is, they may not alter the amino acids encoded by the polynucleotide. Where alterations are limited to silent changes of this type, a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below. With reference to polypeptides generally, differences are limited so that the sequences of the reference and the variant are closely similar overall and, in many regions, identical. A variant and reference polypeptide may differ in amino acid sequence by one or more substitutions, additions, deletions, fusions and truncations, which may be present in any combination.

DETAILED DESCRIPTION OF THE INVENTION

This invention relates, in part, to genetic constructs useful for the temporal and/or spatial expression of cytokinin genes in seed and to associated polynucleotides and polypeptides; variants and derivatives of these polynucleotides and polypeptides; processes for making these polynucleotides and these polypeptides, and their variants and derivatives; agonists and antagonists of the polypeptides; and uses of these polynucleotides, polypeptides, variants, derivatives, agonists and antagonists. In particular, in these and in other regards, the invention relates to polynucleotides and polypeptides of the cytokinin metabolic pathway, most particularly the enzymes ipt and cytokinin oxidase and genes encoding same.

As mentioned above, it is an object of this invention to provide the reagents necessary for the development of transgenic plants characterized by enhanced levels of cytokinin. As used herein, the phrase "enhanced levels of cytokinin" is a relative one and refers to the levels of cytokinin in a control plant without the cytokinin-affecting transgene as compared to a plant with such a functioning transgene. The relative levels may also be measured employing only the transgenic plant but measured in the presence and absence of expression of the subject transgene. Accordingly, any structural gene, the regulated expression of which has the effect of enhancing the effective levels of cytokinin in plants, particularly seeds, is useful for the practice of this invention. Genes that direct the expression of proteins that act to increase the biosynthesis of cytokinin (e.g., ipt or tzs) or genes encoding cytokinin degrading enzymes, the expression of which is inhibited, are the preferred genes for the practice of this invention. However, the use of other genes is contemplated by this invention. For example, the effective levels of cytokinins may be reduced by cytokinin-binding molecules forming inactive or less-active conjugates. Thus gene products that act to release cytokinins from such conjugates (e.g., the product of the RoIC gene or β-glucosidase) are also useful. In addition to genes that affect the absolute levels of cytokinin, genes that affect the ratio of cytokinin to auxin are also useful. Auxin-lowering genes such as iaa-1 and gene-5 may also be employed in the practice of this invention.

As mentioned above, the present invention relates to novel constructions of cytokinin metabolic polypeptides and polynucleotides encoding same, among other things, as described in greater detail below. The polypeptides particularly useful for the practice of this invention include, but are not limited to, ipt and cytokinin oxidase.

The nucleic acids and fragments thereof encoding the above-mentioned enzymes are useful to generate enzyme-producing transgenics. For example, a single gene or gene fragment (or combinations of several genes) may be incorporated into an appropriate expression cassette (using for example the globulin-1 [glb1] promoter for embryo-preferred expression, or the 27 kd gamma zein promoter for endosperm-preferred expression in seed) and transformed into corn along with an appropriate selectable marker (such as the BAR and PAT genes).

In certain situations it may be preferable to silence certain genes, such as the cytokinin oxidase. Relevant literature describing the application of homology-dependent gene silencing include: Jorgensen, *Trends Biotechnol.* 8 (12): 340–344 (1990); Flavell, *Proc. Nat'l. Acad. Sci. (USA)* 91:3490–3496 (1994); Finnegan et al., *Bio/Technology* 12: 883–888 (1994); Neuhuber et al., *Mol. Gen. Genet.* 244: 230–241 (1994). Alternatively, another approach to gene silencing can be with the use of antisense technology (Rothstein et al. in *Plant Mol. Cell. Biol.* 6:221–246 (1989).

Polynucleotides

In accordance with one aspect of the present invention, there is provided the isolated polynucleotide of SEQ ID NO.: 1, which encodes the cytokinin metabolic enzyme maize cytokinin oxidase, having the deduced amino acid sequence shown herein as SEQ. I.D. NO.: 2. The isolated polynucleotide encoding ipt (isopentenyl transferase), as provided at Molecular and General Genetics 216:388–394 (1989), and its deduced amino acid sequence, are also contemplated by this invention.

Using the information provided herein, such as the polynucleotide sequences set out below, a polynucleotide of the present invention encoding cytokinin metabolic enzyme polypeptides may be obtained using standard cloning and screening procedures. To obtain the polynucleotide encoding the protein using the DNA sequences given below, oligonucleotide primers can be synthesized that are complementary to the known polynucleotide sequence. These primers can then be used in PCR to amplify the polynucleotide from template derived from mRNA or genomic DNA isolated from the desired source material. The resulting amplified products can then be cloned into commercially available cloning vectors, such as the TA series of vectors from InVitrogen. By sequencing the individual clones thus identified with sequencing primers designed from the original sequence, it is then possible to extend the sequence in both directions to determine the full gene sequence. Such sequencing is performed using denatured double stranded DNA prepared from a plasmid clone. Suitable techniques are described by Maniatis, T., Fritsch, E. F. and Sambrook, J. in MOLECULAR CLONING, A Laboratory Manual (2nd edition 1989 Cold Spring Harbor Laboratory. See Sequencing Denatured Double-Stranded DNA Templates 13.70.

Isolation of ipt Gene:

The isopentenyl transferases (ipts) of the present invention may be obtained from the following sources: *Agrobacterium, Psuedomonas savastano, Rhodococcus* and *Erwinia*.

The complete sequence of an ipt gene is provided in Strabala, T. J., et al., *Isolation and characterization of an ipt gene from the Ti plasmid Bo542*, Mol. Gen. Genet. 216, 388–94 (1989). A copy of such gene can be prepared synthetically employing DNA synthesis protocols well known to those skilled in the art of gene synthesis. Alternatively, a copy of the gene may be isolated directly from an ipt-gene-harboring organism by PCR cloning. Briefly, PCR primers preferably containing convenient restriction endonuclease sites are constructed. Two useful primers are shown below:

SEQ ID NO: 3 (Upper primer with Bam HI site)
5'caucaucaucauggatccaccaatggatctacgtctaattttcggtccaac 3'
SEQ ID NO:4 (Lower primer with Hpal site)
5'cuacuacuacuagttaactcacattcgaaatggtggtccttc 3'

The introduced restriction sites are bolded. The portion of the primer that binds to the template extends from nucleotides 22 and 19 to the 3' terminus, respectively. A BamHI site "ggatcc" (bolded) and a Kozak consensus sequence were introduced before the start codon and a Hpal site "gttaac" (also bolded) was introduced after the stop. Following is a schematic showing how the primers attach to the published Sequence.

35 seconds, 65° C. for 1 minute, and 72° C. for 1 minute. Finalize reaction by dwelling for 10 minutes at 72° C. and allowing to soak at 6° C. PCR product was then cloned into DH5α cells using a kit made by Life Technologies according to manufacturer's instructions. DNA was extracted from putative transformants, cut with BamHI and Hpal, and run on gel to confirm transformation. This insert was then gel purified and transformed into a convenient expression vector, such as 7921 vector DNA containing a Ubi promoter and pinII terminator.

A preferred DNA sequence is provided in Molecular and General Genetics 216:388–394 (1989). It contains an open reading frame encoding a protein of 239 amino acid residues, with a deduced molecular weight of about 26.3 kDa (Calculated as the number of amino acid residues×110).

Isolation of Maize Cytokinin Oxidase Gene, Cytox 1–2:

Another preferred DNA sequence is set out below as SEQ. I.D. NO: 1. It contains an open reading frame encoding a protein of about 535 amino acid residues, SEQ ID NO.:2, with a deduced molecular weight of about 58.9 kDa (Calculated as the number of amino acid residues×110). A copy of cytokinin oxidase can be prepared synthetically employ-

```
BamHI

5'caucaucaucauggatccaccaatggatctacgtctaattttcggtccaac aatggatctacgtctaattttcggtccaacttgcacagg aaagacatcgactgcgatagctcttgcccagcagactggcctcccagtcctctcgctcgatcgcgtccaatgctgtcctcaactatcaaccg gaagcgggcgaccaacagtggaagaactgaaaggaacgactcgtctgtaccttgatgatcgcccttttggtaaagggtatcattacagccaa gcaagctcatgaacggctcattgcggaggtgcacaatcacgaggccaaaggcgggcttattcttgagggaggatctatctcgttgctcaggt gcatggcgcaaagtcgttattggaacgcggattttcgttggcatattattcgcaacgagttagcagacgaggagagcttcatgagcgtggcc aagaccagagttaagcagatgttacgccctctgcaggtctttctattatccaagagttggttcaactttggagggagcctcggctgaggccc atactggaagggatcgatggatatcgatatgcctgctatttgctacccagaaccagatcacgcccgatatgctattgcagctcgacgcagat atggagaataaattgattcacggtatcgctcaggagtttctaatccatgcgcgtcgacaggaacagaaattccctttggtgggcgcgacagct gtcgaagcgtttgaaggaccaccatttcgaatgtga 3'cctggtggtaaagcttacactcattgaucaucaucauc Hpal]
```

The *Agrobacterium tumefaciens* strain carrying the tumor-inducing plasmid pTi Bo542 was obtained (See Guyon, P., et al.,*Agropine in null-type crown gall tumors: Evidence for generality of the opine concept*, Proceedings of the National Academy of Sciences (U.S.) 77(5): 2693–97 (1980); Chilton, W. S., et al. *Absolute stereochemistry of leucinopine, a crown gall opine*, Phytochemistry (Oxford) 24(2): 221–24 (1985); Strabala, T. J., et al., *Isolation and characterization of an ipt gene from the Ti plasmid Bo542*, Molecular & General Genetics 216: 388–94 (1989)) and live bacteria were used for the PCR template. Standard PCR conditions were used. An example of such conditions follows: Volume per reaction of 100 $\mu$L, with 0.5 $\mu$L of 10 ng/$\mu$L target plasmid, 0.05 Unit/$\mu$L Taq Polymerase, 0.5 $\mu$M each of primers, 0.8 mM dNTP's 1× Buffer in a thin walled tube. Mix reagents, keep on ice. Add target plasmid to tube and then add the 100 $\mu$L of reaction mix to each tube. Pre-incubate in a thermocycler at 95° C. for 3 minutes. Then cycle five times at 95° C. for 35 seconds, 55° C. for 1 minute, and 72° C. for 1 minute. Follow with 30 cycles at 95° C. for ing DNA synthesis protocols well known to those skilled in the art of gene synthesis. Alternatively, a copy of the gene may be isolated directly from a cytokinin oxidase harboring organism by PCR cloning. A maize cytokinin oxidase gene (ckx1) was cloned by Roy Morris of the University of Missouri and the sequence deposited in Genbank. (Morris et al., 1999. Isolation of a gene encoding a glycosylated cytokinin oxidase from maize. Biochem. Biophys. Res. Commun. 255(2):328–333. See also Houba-Herin et al., 1999. Cytokinin oxidase from *Zea mays*: purification, cDNA cloning and expression in moss protoplasts. Plant J. (6): 615–626.) PCR primers preferably containing convenient restriction endonuclease sites are constructed: Two useful primers are shown below:
SEQ ID NO.: 5:
5' CATGCCATGGCGGTGGTTTATTACCTGCT 3' (with NcoI site at 5' end)
SEQ ID NO.: 6:
5' CGGGATCCTCATCATCAGTTGAAGATGTCCT 3' (with BamHI site at 3' end)

These primers were designed against the sequence of ckx1 and reverse transcriptase PCR (RT-PCR) was utilized to isolate cytokinin oxidase genes from several different tissues of developing maize kernels. DNA fragments were amplified from the following tissues: 10 DAP, 13 DAP, 18 DAP, and 20 DAP endosperms; as well as 10 DAP, 18 DAP, and 20 DAP embryos, where DAP is days after pollination. Fragments from all tissues migrated to 1.6 Kb in the gel, which is equal to that of the published sequence. We selected one of the fragments (from 18 DAP embryos) and sequenced the DNA. This fragment is referred to herein as Cytox1–2 and its full-length sequence is set out below in SEQ ID NO.: 1. At the amino acid level, there is a 98% homology between the ckx1 gene and cytox1–2, therefore, one of skill in the art would recognize that cytox1–2 is a cytokinin oxidase gene from maize.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the antisense strand.

The coding sequence which encodes the polypeptide may be identical to the coding sequence of the polynucleotides shown below. It also may be a polynucleotide with a different sequence, which, as a result of the redundancy (degeneracy) of the genetic code, encodes the polypeptides shown below. As discussed more fully below, these alternative coding sequences are an important source of sequences for codon optimization.

Polynucleotides of the present invention which encode the polypeptides listed below may include, but are not limited to, the coding sequence for the mature polypeptide, by itself; the coding sequence for the mature polypeptide and additional coding sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to, non-coding 5' and 3' sequences, such as the transcribed, non-translated sequences that play a role in transcription (including termination signals, for example), ribosome binding, mRNA stability elements, and additional coding sequences which encode additional amino acids, such as those which provide additional functionalities.

The DNA may also comprise promoter regions which function to direct the transcription of the mRNA encoding heterologous cytokinin metabolic enzymes of this invention. Heterologous is defined as a sequence that is not naturally occurring with the promoter sequence. While the nucleotide sequence is heterologous to the promoter sequence, it may be homologous (native) or heterologous (foreign) to the plant host.

Furthermore, the polypeptide may be fused to a marker sequence, such as a peptide, which facilitates purification of the fused polypeptide. In certain embodiments of this aspect of the invention, the marker sequence is a hexa-histidine peptide, such as the tag provided in the pQE vector (Qiagen, Inc.) and the pET series of vectors (Novagen), among others, many of which are commercially available. As described in Gentz et al., *Proc. Nat'l. Acad. Sci., (USA)* 86:821–824 (1989), for instance, hexa-histidine provides for convenient purification of the fusion protein. The HA tag may also be used to create fusion proteins and corresponds to an epitope derived of influenza hemagglutinin protein, which has been described by Wilson et al., *Cell* 37:767 (1984), for instance.

In accordance with the foregoing, the term "polynucleotide encoding a polypeptide" as used herein encompasses polynucleotides which include a sequence encoding a polypeptide of the present invention, particularly cytokinin biosynthetic enzymes having the amino acid sequences set out below. The term encompasses polynucleotides that include a single continuous region or discontinuous regions encoding the polypeptide (for example, interrupted by integrated phage or insertion sequence or editing) together with additional regions, that also may contain coding and/or non-coding sequences.

The present invention further relates to variants of the present polynucleotides which encode for fragments, analogs and derivatives of the polypeptides having the deduced amino acid sequence below. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequences set out below; variants, analogs, derivatives and fragments thereof.

Further particularly preferred in this regard are polynucleotides encoding cytokinin biosynthetic enzyme variants, analogs, derivatives and fragments, and variants, analogs and derivatives of the fragments, which have the amino acid sequences below in which several, a few, 1 to 10, 1 to 5, 1 to 3, 2, 1 or no amino acid residues are substituted, deleted or added, in any combination. Especially preferred among these are silent substitutions, additions and deletions, which do not alter the properties and activities of the cytokinin biosynthetic enzymes. Also especially preferred in this regard are conservative substitutions. Most highly preferred are polynucleotides encoding polypeptides having the amino acid sequence below, without substitutions.

Further preferred embodiments of the invention are polynucleotides that are greater than 79%, preferably at least 80%, more preferably at least 85% identical to a polynucleotide encoding the ipt polypeptide having the amino acid sequence set out below, and polynucleotides which are complementary to such polynucleotides. Among these particularly preferred polynucleotides, those with at least 90%, 95%, 98% or at least 99% are especially preferred.

Particularly preferred embodiments in this respect, moreover, are polynucleotides which encode polypeptides which retain substantially the same, or even exhibit a increase in, biological function or activity as the mature polypeptide encoded by the polynucleotides set out below.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

The terms "stringent conditions" or "stringent hybridization conditions" include reference to conditions under which a probe will hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA—DNA hybrids, the $T_m$ can be approximated from the equation of Meinkoth and Wahl, *Anal. Biochem.*, 138:267–284 (1984): $T_m$=81.5° C.+16.6 (log M)+0.41 (% GC)–0.61 (% form) –500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. Hybridization and/or wash conditions can be applied for at least 10, 30, 60, 90, 120, or 240 minutes. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel, et al., Eds., Greene Publishing and Wiley-Interscience, New York (1995).

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding cytokinin biosynthetic enzymes and to isolate cDNA and genomic clones of other genes that have a high sequence similarity to the genes. Such probes generally will comprise at least 15 bases. Preferably, such probes will have at least 30 bases and may have at least 50 bases. Particularly preferred probes will have at least 30 bases and will have 50 bases or less.

The polynucleotides and polypeptides of the present invention may be employed as research reagents and materials for discovery of high cytokinin transgenic corn plants. The polynucleotides of the invention that are oligonucleotides derived from the sequences below may be used as PCR primers in the process herein described to determine whether or not the genes identified herein in whole or in part are transcribed in cytokinin accumulating tissue.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences, may be an inactive form of the polypeptide. When prosequences are removed, such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Polypeptides

The present invention further relates to polypeptides that have the deduced amino acid sequences below.

The invention also relates to fragments, analogs and derivatives of these polypeptides. The terms "fragment," "derivative" and "analog", when referring to the polypeptides, mean a polypeptide which retains essentially the same biological function or activity as such polypeptide. Fragments, derivatives and analogs that retain at least 90% of the activity of the native cytokinin biosynthetic enzymes are preferred. Fragments, derivatives and analogs that retain at least 95% of the activity of the native polypeptides are preferred. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments it is a recombinant polypeptide.

The fragment, derivative or analog of the polypeptides below may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be obtained by those of ordinary skill in the art, from the teachings herein.

Among the particularly preferred embodiments of the invention in this regard are polypeptides having the amino acid sequence of cytokinin biosynthetic enzymes set out below, variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Further particularly preferred in this regard are variants, analogs, derivatives and fragments, and variants, analogs and derivatives of the fragments, having the amino acid sequence below, in which several, a few, 1 to 10, 1 to 5, 1 to 3, 2, 1 or no amino acid residues are substituted, deleted or added, in any combination. Especially preferred among these are silent substitutions, additions and deletions, which do not alter the properties and activities of the cytokinin biosynthetic enzymes. Also especially preferred in this regard are conservative substitutions. Most highly preferred are polypeptides having the amino acid sequences below without substitutions.

The polypeptides and polynucleotides of the present invention are preferably provided in an isolated form, and may be purified to homogeneity.

Vectors, Host Cells, Expression

The present invention also relates to vectors comprising the polynucleotides of the present invention, host cells that incorporate the vectors of the invention and the production of polypeptides of the invention by recombinant techniques in a spatially and temporally defined manner.

Vectors

In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsidated virus by well known techniques for infection and transduction. Viral vectors may be replication competent or replication defective. In the latter case, viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors are supplied by the host, supplied by a complementing vector or supplied by the vector itself upon introduction into the host.

In certain preferred embodiments in this regard, the vectors provide for preferred expression. Such preferred expression may be inducible expression or temporally limited or restricted to predominantly certain types of cells or any combination of the above. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids and binaries used for *Agrobacterium*-mediated transformations. All may be used for expression in accordance with this aspect of the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Useful plant binaries vectors include BIN19 and its derivatives available from Clontech. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention, several of which are disclosed in more detail below.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as transcription factors, repressor binding sites and termination, among others. For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers. Additional enhancers useful in the invention to increase transcription of the introduced DNA segment, include, inter alia, viral enhancers like those within the 35S promoter, as shown by Odell et al., *Plant Mol. Biol.* 10:263–72 (1988), and an enhancer from an opine gene as described by Fromm et al., *Plant Cell* 1:977 (1989).

Termination regions also facilitate effective expression by ending transcription at appropriate points. Useful terminators for practicing this invention include, but are not limited to, pinII (See An et al., Plant Cell 1(1):115–122 (1989)), glb1 (See Genbank Accession #L22345), gz (See gzw64a terminator, Genbank Accession #S78780), and nos.

Among known eukaryotic promoters suitable for generalized expression are the CMV immediate early promoter, the HSV thymidine kinase promoter, the early and late SV40 promoters, the promoters of retroviral LTRs, such as those of the Rous sarcoma virus ("RSV"), metallothionein promoters, such as the mouse metallothionein-1 promoter and various plant promoters, such as globulin-1. When available, the native promoters of the cytokinin biosynthetic enzyme genes may be used. Representatives of prokaryotic promoters include the phage lambda PL promoter, the *E. coli* lac, trp and tac promoters to name just a few of the well-known promoters.

With respect to plants, examples of seed-preferred promoters include promoters of seed storage proteins which express these proteins in seeds in a highly regulated manner (Thompson, et al.; *BioEssays;* 10:108; (1989), incorporated herein in its entirety by reference), such as, for dicotyledonous plants, a bean β-phaseolin promoter, a napin promoter, a β-conglycinin promoter, and a soybean lectin promoter. For monocotyledonous plants, promoters useful in the practice of the invention include, but are not limited to, a maize 15 kD zein promoter, a 22 kD zein promoter, a 27 Kd γ-zein promoter (such as gzw64A promoter, see Genbank Accession #S78780), a waxy promoter, a shrunken-1 promoter, a globulin 1 promoter (See Genbank Accession # L22344), an ltp2 promoter (Kalla, et al., Plant Journal 6:849–860 (1994); U.S. Pat. No. 5,525,716), cim1 promoter (see co-pending U.S. patent application Ser. No. 09/377,648), and the shrunken-2 promoter. However, other promoters useful in the practice of the invention are known to those of skill in the art such as nucellain promoter (See C. Linnestad, et al., *Nucellain, A Barley Homolog of the Dicot Vacuolar—Processing Proteasem Is Localized in Nucellar Cell Walls*, Plant Physiol. 118:1169–80 (1998), kn1 promoter (See S. Hake and N. Ori, *The Role of knotted1 in Meristem Functions, B8: INTERACTIONS AND INTERSECTIONS IN PLANT PATHWAYS*, COEUR D'ALENE, IDAHO, KEYSTONE SYMPOSIA, Feb. 8–14, 1999, at 27.), and maize end 1 and end 2 promoters (See U.S. provisional patent application 60/098,230, filed Aug. 28, 1998 and U.S. patent application Ser. No. 09/383,543, filed Aug. 26, 1999). See also U.S. patent application 60/163,114, filed Nov. 2, 1999, and 60/155,859, filed Sep. 24, 1999. Spatially acting promoters such as glb1, an embryo-preferred promoter, or gamma zein, an endosperm-preferred promoter (such as BET1, See G. Hueros, et al., *Molecular Characterization of BET-1, a Gene Expressed in the Endosperm Transfer Cells of Maize*, Plant Cell 7:747–67 (June 1995).), are particularly useful. The use of temporally acting promoters is also contemplated by this invention. Promoters that act from 0–25 days after pollination (DAP) are preferred, as are those acting from 4–21, 4–12, or 8–12 DAP. In this regard, promoters such as cim1 and ltp2 are preferred. Promoters that act from −14 to 0 days after pollination can also be used, such as SAG12 (See WO 96/29858, Richard M. Amasino, published 3 Oct. 1996.) and ZAG1 or ZAG2 (See R. J. Schmidt, et al., *Identification and Molecular Characterization of ZAG1, the Maize Homolog of the Arabidopsis Floral Homeotic Gene AGAMOUS*, Plant-Cell 5(7): 729–37 (July 1993)).

Examples of suitable promoters for generalized expression in plants are the promoter for the small subunit of ribulose-1,5-bis-phosphate carboxylase, promoters from tumor-inducing plasmids of *Agrobacterium tumefaciens*, such as the nopaline synthase and octopine synthase promoters, and viral promoters such as the cauliflower mosaic virus (CaMV) 19S and 35S promoters or the figwort mosaic virus 35S promoter.

It will be understood that numerous promoters not mentioned are suitable for use in this aspect of the invention, are well known and readily may be employed by those of skill in the manner illustrated by the discussion and the examples herein. For example, this invention contemplates using, when appropriate, the native cytokinin biosynthetic enzyme promoters to drive the expression of the enzyme in a recombinant environment.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing *E. coli* and other prokaryotes. Kanamycin and herbicide resistance genes (PAT and BAR) are generally useful in plant systems.

Selectable marker genes, in physical proximity to the introduced DNA segment, are used to allow transformed cells to be recovered by either positive genetic selection or screening. The selectable marker genes also allow for maintaining selection pressure on a transgenic plant population, to ensure that the introduced DNA segment, and its controlling promoters and enhancers, are retained by the transgenic plant.

Many of the commonly used positive selectable marker genes for plant transformation have been isolated from bacteria and code for enzymes that metabolically detoxify a selective chemical agent which may be an antibiotic or a herbicide. Other positive selection marker genes encode an altered target which is insensitive to the inhibitor.

A preferred selection marker gene for plant transformation is the BAR or PAT gene, which is used with the selecting agent bialaphos. Spencer et al., J. Thero. Appl'd Genetics 79:625–631 (1990). Another useful selection marker gene is the neomycin phosphotransferase II (nptII) gene, isolated from Tn5, which confers resistance to kanamycin when placed under the control of plant regulatory signals. Fraley et al., Proc. Nat'l Acad. Sci. (USA) 80:4803 (1983). The hygromycin phosphotransferase gene, which confers resistance to the antibiotic hygromycin, is a further example of a useful selectable marker. Vanden Elzen et al., Plant Mol. Biol. 5:299 (1985). Additional positive selectable markers genes of bacterial origin that confer resistance to antibiotics include gentamicin acetyl transferase, streptomycin phosphotransferase, aminoglycoside-3'-adenyl transferase and the bleomycin resistance determinant. Hayford et al., Plant Physiol. 86:1216 (1988); Jones et al., Mol. Gen. Genet. 210:86 (1987); Svab et al., Plant Mol. Biol. 14:197 (1990); Hille et al., Plant Mol. Biol. 7:171 (1986).

Other positive selectable marker genes for plant transformation are not of bacterial origin. These genes include mouse dihydrofolate reductase, plant 5-enolpyruvylshikimate-3-phosphate synthase and plant acetolactate synthase. Eichholtz et al., Somatic Cell Mol. Genet. 13:67 (1987); Shah et al., Science 233:478 (1986); Charest et al., Plant Cell Rep. 8:643 (1990).

Another class of useful marker genes for plant transformation with the DNA sequence requires screening of presumptively transformed plant cells rather than direct genetic selection of transformed cells for resistance to a toxic substance such as an antibiotic. These genes are particularly useful to quantitate or visualize the spatial pattern of expression of the DNA sequence in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase. Jefferson, Plant Mol. Biol. Rep. 5:387 (1987); Teeri et al., EMBO J. 8:343 (1989); Koncz et al., Proc. Nat'l Acad. Sci. (USA) 84:131 (1987); De Block et al., EMBO J. 3:1681 (1984). Another approach to the identification of relatively rare transformation events has been use of a gene that encodes a dominant constitutive regulator of the Zea mays anthocyanin pigmentation pathway(Ludwig et al., Science 247:449 (1990)).

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. The sequence may be inserted in a forward or reverse orientation. Procedures for restriction and ligation that can be used to this end are well known and routine to those of skill. Suitable procedures in this regard, and for constructing expression vectors using alternative techniques, which also are well known and routine to those of skill, are set forth in great detail in Sambrook et al., MOLECULAR CLONING, A LABORATORY MANUAL, 2nd Ed.; Cold Spring Harbor Laboratory Press, Cold Spring Harbor, N.Y. (1989).

A polynucleotide of the invention, encoding the heterologous structural sequence of a polypeptide of the invention, generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiation codon. Also, generally, there will be a translation stop codon at the end of the polypeptide and there will be a polyadenylation signal in constructs for use in eukaryotic hosts. Transcription termination signal appropriately disposed at the 3' end of the transcribed region may also be included in the polynucleotide construct.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. The present invention also relates to host cells containing the above-described constructs discussed. The host cell can be a higher eukaryotic cell, such as a mammalian or plant cell, or a lower eukaryotic cell, such as a yeast cell, or the host cell can be a prokaryotic cell, such as a bacterial cell.

Introduction of the construct into the host cell can be effected by calcium phosphate transfection, DEAE-dextran mediated transfection, microinjection, cationic lipid-mediated transfection, electroporation, transduction, scrape loading, ballistic introduction, infection or other methods. Such methods are described in many standard laboratory manuals, such as Davis et al., BASIC METHODS IN MOLECULAR BIOLOGY, (1986) and Sambrook et al., MOLECULAR CLONING: A LABORATORY MANUAL, 2nd Ed., Cold Spring Harbor Laboratory Press, Cold Spring Harbor, N.Y. (1989).

Representative examples of appropriate hosts include bacterial cells, such as streptococci, staphylococci, E. coli, streptomyces and Salmonella typhimurium cells; fungal cells, such as yeast cells and Aspergillus cells; insect cells such as Drosophila S2 and Spodoptera Sf9 cells; animal cells such as CHO, COS and Bowes melanoma cells; and plant cells. The plants cells may be derived from a broad range of plant types, particularly monocots such as the species of the Family Graminiae including Sorghum bicolor and Zea mays. The isolated nucleic acid and proteins of the present invention can also be used in species from the genera: Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, and Triticum.

Hosts for a great variety of expression constructs are well known, and those of skill will be enabled by the present disclosure readily to select a host for expressing a polypeptide in accordance with this aspect of the present invention.

The engineered host cells can be cultured in conventional nutrient media, which may be modified as appropriate for, inter alla, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

Mature proteins can be expressed in mammalian cells, yeast, bacteria, or other cells under the control of appropriate promoters. Cell-free translation systems can also be employed to produce such proteins using RNAs derived from the DNA constructs of the present invention.

Following transformation of a suitable host strain and growth of the host strain to an appropriate cell density, where the selected promoter is inducible it is induced by appropriate means (e.g., temperature shift or exposure to chemical inducer) and cells are cultured for an additional period.

Cells typically then are harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents; such methods are well know to those skilled in the art.

Plant Transformation Methods:

Isolated nucleic acid acids of the present invention can be introduced into plants according to techniques known in the art. Generally, recombinant expression cassettes as described above and suitable for transformation of plant cells are prepared. Techniques for transforming a wide variety of higher plant species are well known and described in the technical, scientific, and patent literature. See, for example, Weising et al., *Ann. Rev. Genet.* 22: 421–477 (1988). For example, the DNA construct may be introduced directly into the genomic DNA of the plant cell using techniques such as electroporation, PEG poration, particle bombardment, silicon fiber delivery, or microinjection of plant cell protoplasts or embryogenic callus. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using polyethylene glycol precipitation is described in Paszkowski et al., *Embo J.* 3: 2717–2722 (1984). Electroporation techniques are described in Fromm et al., *Proc. Natl. Acad. Sci* (USA) 82: 5824 (1985). Ballistic transformation techniques are described in Klein et al., *Nature* 327: 70–73 (1987) and by Tomes, D. et al., IN: Plant Cell, Tissue and Organ Culture: Fundamental Methods, Eds. O. L. Gamborg and G. C. Phillips, Chapter 8, pgs. 197–213 (1995). (See also Tomes et al., U.S. Pat. No. 5,886,244.) *Agrobacterium tumefaciens-meditated* transformation techniques are well described in the scientific literature. See, for example Horsch et al., *Science* 233: 496–498 (1984), and Fraley et al., *Proc. Natl. Acad. Sci*(USA) 80: 4803 (1983). Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller In: Genetic Engineering, vol. 6, P W J Rigby, Ed., London, Academic Press, 1987; and Lichtenstein, C. P., and Draper, J, In: DNA Cloning, Vol. II, D. M. Glover, Ed., Oxford, IRI Press, 1985), Application PCT/US87/02512 (WO 88/02405 published Apr. 7, 1988) describes the use of *A. rhizogenes* strain A4 and its R1 plasmid along with *A. tumefaciens* vectors pARC8 or pARC16 (2) liposome-mediated DNA uptake (see, e.g., Freeman et al., Plant Cell Physiol. 25: 1353, 1984), (3) the vortexing method (see, e.g., Kindle, *Proc. Nat'l. Acad. Sci.*(USA) 87: 1228, (1990).

DNA can also be introduced into plants by direct DNA transfer into pollen as described by Zhou et al., *Methods in Enzymology,* 101:433 (1983); D. Hess, *Intern. Rev. Cytol.,* 107:367 (1987); Luo et al., *Plant Mol. Biol. Reporter,* 6:165(1988). Expression of polypeptide coding genes can be obtained by injection of the DNA into reproductive organs of a plant as described by Pena et al., *Nature* 325:274 (1987). DNA can also be injected directly into the cells of immature embryos and the rehydration of desiccated embryos as described by Neuhaus et al., *Theor. Appl. Genet.,* 75:30 (1987); and Benbrook et al., in *Proceedings Bio Expo.* 1986, Butterworth, Stoneham, Mass., pp. 27–54 (1986). A variety of plant viruses that can be employed as vectors are known in the art and include cauliflower mosaic virus (CaMV), geminivirus, brome mosaic virus, and tobacco mosaic virus.

Regeneration of Transformed Plants

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced together with a polynucleotide of the present invention. For transformation and regeneration of maize see, Gordon-Kamm et al., *The Plant Cell,* 2:603–618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture,* Macmillilan Publishing Company, New York, pp. 124–176 (1983); and Binding, *Regeneration of Plants, Plant Protoplasts,* CRC Press, Boca Raton, pp. 21–73 (1985).

The regeneration of plants containing the foreign gene introduced by *Agrobacterium* from leaf explants can be achieved as described by Horsch et al., *Science,* 227:1229–1231 (1985). In this procedure, transformants are grown in the presence of a selection agent and in a medium that induces the regeneration of shoots in the plant species being transformed as described by Fraley et al., *Proc. Nat'l. Acad. Sci.* (*U.S.A*), 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38: 467–486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook*, Freeling and Walbot, Eds., Springer, N.Y. (1994); *Corn and Corn Improvement*, $3^{rd}$ edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed-propagated crops, mature transgenic plants can be self-crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

It is also expected that the transformed plants will be used in traditional breeding programs, including TOPCROSS pollination systems as disclosed in U.S. Pat. No. 5,706,603 and U.S. Pat. No. 5,704,160, the disclosure of each of which is incorporated herein by reference.

Polynucleotide Assays

This invention is also related to the use of the cytokinin biosynthetic enzyme polynucleotides in markers to assist in a breeding program, as described for example in PCT publication US89/00709. The DNA may be used directly for detection or may be amplified enzymatically by using PCR (Saiki et al., *Nature* 324:163–166 (1986)) prior to analysis. RNA or cDNA may also be used in the same ways. As an example, PCR primers complementary to the nucleic acid encoding the cytokinin biosynthetic enzymes can be used to identify and analyze cytokinin biosynthetic enzyme presence and expression. Using PCR, characterization of the gene present in a particular tissue or plant variety may be made by an analysis of the genotype of the tissue or variety. For example, deletions and insertions can be detected by a change in size of the amplified product in comparison to the genotype of a reference sequence. Point mutations can be identified by hybridizing amplified DNA to radiolabeled cytokinin biosynthetic enzyme RNA or alternatively, radiolabeled cytokinin biosynthetic enzyme antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent tags.

Genetic typing of various varieties of plants based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science*, 230:1242 (1985)).

Sequence changes at specific locations also may be revealed by nuclease protection assays, such as RNase and S1 protection or the chemical cleavage method (e.g., Cotton et al., *Proc. Nat'l. Acad. Sci.*, (*USA*), 85:4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

A mutation may be ascertained, for example, by a DNA sequencing assay. Samples are processed by methods known in the art to capture the RNA. First strand cDNA is synthesized from the RNA samples by adding an oligonucleotide primer consisting of sequences which hybridize to a region on the mRNA. Reverse transcriptase and deoxynucleotides are added to allow synthesis of the first strand cDNA. Primer sequences are synthesized based on the DNA sequences of the cytokinin biosynthetic enzymes of the invention. The primer sequence is generally comprised of at least 15 consecutive bases, and may contain at least 30 or even 50 consecutive bases.

Cells carrying mutations or polymorphisms in the gene of the present invention may also be detected at the DNA level by a variety of techniques. The DNA may be used directly for detection or may be amplified enzymatically by using PCR (Saiki et al., Nature, 324:163–166 (1986)) prior to analysis. RT-PCR can also be used to detect mutations. It is particularly preferred to use RT-PCR in conjunction with automated detection systems, such as, for example, GeneScan. RNA or cDNA may also be used for the same purpose, PCR or RT-PCR. As an example, PCR primers complementary to the nucleic acid encoding cytokinin biosynthetic enzymes can be used to identify and analyze mutations. Examples of representative primers are shown below in Table 1. For example, deletions and insertions can be detected by a change in size of the amplified product in comparison to the normal genotype. Point mutations can be identified by hybridizing amplified DNA to radiolabeled RNA, or alternatively, radiolabeled antisense DNA sequences. While perfectly matched sequences can be distinguished from mismatched duplexes by RNase A digestion or by differences in melting temperatures, preferably point mutations are identified by sequence analysis. Primers used for detection of mutations or polymorphisms in the ipt gene:

5'GCGTCCAATGCTGTCCTCMCTA3' (SEQ. ID. NO: 10)

5'GCTCTCCTCGTCTGCTMCTCGT3' (SEQ. ID. NO: 11)

The above primers may be used for amplifying cytokinin biosynthetic enzyme cDNA or genomic clones isolated from a sample derived from an individual plant. The invention also provides the primers above with 1, 2, 3 or 4 nucleotides removed from the 5' and/or the 3' end. The primers may be used to amplify the gene isolated from the individual such that the gene may then be subject to various techniques for elucidation of the DNA sequence. In this way, mutations in the DNA sequence may be identified.

Polypeptide Assays

The present invention also relates to diagnostic assays such as quantitative and diagnostic assays for detecting levels of cytokinin biosynthetic enzymes in cells and tissues, including determination of normal and abnormal levels. Thus, for instance, a diagnostic assay in accordance with the invention for detecting expression of cytokinin biosynthetic enzymes compared to normal control tissue samples may be used to detect unacceptable levels of expression. Assay techniques that can be used to determine levels of polypeptides of the present invention in a sample derived from a plant source are well-known to those of skill in the art. Such assay methods include radioimmunoassays, competitive-binding assays, Western Blot analysis and ELISA assays. Among these, ELISAs frequently are preferred. An ELISA assay initially comprises preparing an antibody specific to the polypeptide, preferably a monoclonal antibody. In addition, a reporter antibody generally is prepared which binds to the monoclonal antibody. The reporter antibody is attached to a detectable reagent such as a radioactive, fluorescent or enzymatic reagent, in this example horseradish peroxidase enzyme.

To carry out an ELISA, a sample is removed from a host and incubated on a solid support, e.g., a polystyrene dish, that binds the proteins in the sample. Any free protein binding sites on the dish are then covered by incubating with a non-specific protein such as bovine serum albumin. Next, the monoclonal antibody is incubated in the dish, during which time the monoclonal antibodies attach to any cytokinin biosynthetic enzymes attached to the polystyrene dish. Unbound monoclonal antibody is washed out with buffer. The reporter antibody linked to horseradish peroxidase is placed in the dish, resulting in binding of the reporter antibody to any monoclonal antibody bound to cytokinin biosynthetic enzyme. Unattached reporter antibody is then washed out. Reagents for peroxidase activity, including a colorimetric substrate, are then added to the dish. Immobilized peroxidase, linked to cytokinin biosynthetic enzyme through the primary and secondary antibodies, produces a colored reaction product. The amount of color developed in a given time period indicates the amount of cytokinin biosynthetic enzyme present in the sample. Quantitative results typically are obtained by reference to a standard curve.

A competition assay may be employed wherein antibodies specific to cytokinin biosynthetic enzymes are attached to a solid support, and labeled enzyme derived from the host is passed over the solid support. The amount of label detected attached to the solid support can be correlated to a quantity of cytokinin biosynthetic enzyme in the sample.

Antibodies

The polypeptides, their fragments or other derivatives, or analogs thereof, or cells expressing them can be used as immunogens to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal, or by administering the polypeptides to an animal, preferably a nonhuman. The antibody so obtained will then bind the polypeptides itself. In this manner, even a sequence encoding only a fragment of the polypeptide can be used to generate antibodies binding the whole native polypeptide. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler, G. and Milstein, C., Nature 256:495–497 (1975)), the trioma technique, the human B-cell hybridoma technique (Kozbor et al., Immunology Today 4:72 (1983)) and the EBV-hybridoma technique to produce human monoclonal antibodies (Cole et al., pg. 77–96 in *MONOCLONAL ANTIBODIES AND CANCER THERAPY*, Alan R. Liss, Inc. (1985)).

Hybridoma cell lines secreting the monoclonal antibody are another aspect of this invention.

Techniques described for the production of single-chain antibodies (U.S. Pat. No. 4,946,778) can be adapted to produce single-chain antibodies to immunogenic polypeptide products of this invention. Also, transgenic mice, or other organisms such as other mammals, may be used to express humanized antibodies to immunogenic polypeptide products of this invention.

The above-described antibodies may be employed to isolate or identify clones expressing the polypeptide or to purify the polypeptide of the present invention by attachment of the antibody to a solid support for isolation and/or purification by affinity chromatography.

Polypeptide derivatives include antigenically or immunologically equivalent derivatives which form a particular aspect of this invention.

The term 'antigenically equivalent derivative' as used herein encompasses a polypeptide or its equivalent which will be specifically recognized by certain antibodies which, when raised to the protein or polypeptide according to the present invention, interfere with the immediate physical interaction between the antibody and its cognate antigen.

The term "immunologically equivalent derivative" as used herein encompasses a peptide or its equivalent which, when used in a suitable formulation to raise antibodies in a vertebrate, results in antibodies which act to interfere with the immediate physical interaction between the antibody and its cognate antigen.

The polypeptide, such as an antigenically or immunologically equivalent derivative or a fusion protein thereof, is used as an antigen to immunize a mouse or other animal, such as a rat, guinea pig, goat, rabbit, sheep, bovine or chicken. The fusion protein may provide stability to the polypeptide. The antigen may be associated, for example by conjugation, with an immunogenic carrier protein, for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof, may be sufficiently antigenic to improve immunogenicity so as to obviate the use of a carrier.

Alternatively, phage display technology could be utilized to select antibody genes with binding activities towards the polypeptide either from repertoires of PCR amplified v-genes of lymphocytes from humans screened for possessing anti-Fbp or from naive libraries (McCafferty, J. et al., (1990), *Nature* 348:552–554; Marks, J. et al., (1992) *Bio-technology* 10:779–783). The affinity of these antibodies can also be improved by chain shuffling (Clackson, T. et al., (1991) *Nature* 352:624–628).

The antibody should be screened again for high affinity to the polypeptide and/or fusion protein.

As mentioned above, a fragment of the final antibody may be prepared.

The antibody may be either intact antibody of $M_r$ approximately 150,000 or a derivative of it, for example a Fab fragment or a Fv fragment as described in Sierra, A and Pluckthun, A., *Science* 240:1038–1040 (1988). If two antigen binding domains are present, each domain may be directed against a different epitope—termed 'bispecific' antibodies.

The antibody of the invention, as mentioned above, may be prepared by conventional means, for example by established monoclonal antibody technology (Kohler, G. and Milstein, C., *Nature*, 256:495–497 (1975)) or using recombinant means e.g. combinatorial libraries, for example as described in Huse, W. D. et al., *Science* 246:1275–1281 (1989).

Preferably the antibody is prepared by expression of a DNA polymer encoding said antibody in an appropriate expression system such as described above for the expression of polypeptides of the invention. The choice of vector for the expression system will be determined in part by the host, which may be a prokaryotic cell, such as *E. coli* (preferably strain B) or *Streptomyces* sp. or a eukaryotic cell, such as a mouse C127, mouse myeloma, human HeLa, Chinese hamster ovary, filamentous or unicellular fungi or insect cell. The host may also be a transgenic animal or a transgenic plant for example as described in Hiatt, A. et al., *Nature* 340:76–78 (1989). Suitable vectors include plasmids, bacteriophages, cosmids and recombinant viruses, derived from, for example, baculoviruses and vaccinia.

The Fab fragment may also be prepared from its parent monoclonal antibody by enzyme treatment, for example using papain to cleave the Fab portion from the Fc portion.

Cytokinin Biosynthetic Enzyme Binding Molecules and Assays

This invention also provides a method for identification of molecules, such as binding molecules, that bind the cytokinin biosynthetic enzymes. Genes encoding proteins that bind the enzymes, such as binding proteins, can be identified by numerous methods known to those of skill in the art, for example, ligand panning and FACS sorting. Such methods are described in many laboratory manuals such as, for instance, Coligan et al., *Current Protocols in Immunology* 1(2): Chapter 5 (1991).

For instance, expression cloning may be employed for this purpose. To this end, polyadenylated RNA is prepared from a cell expressing the cytokinin biosynthetic enzymes, a cDNA library is created from this RNA, the library is divided into pools, and the pools are transfected individually into cells that are not expressing the enzyme. The transfected cells then are exposed to labeled enzyme. The enzyme can be labeled by a variety of well-known techniques, including standard methods of radio-iodination or inclusion of a recognition site for a site-specific protein kinase. Following exposure, the cells are fixed and binding of enzyme is determined. These procedures conveniently are carried out on glass slides.

Pools are identified of cDNA that produced cytokinin biosynthetic enzyme-binding cells. Sub-pools are prepared from these positives, transfected into host cells and screened as described above. Using an iterative sub-pooling and re-screening process, one or more single clones that encode the putative binding molecule can be isolated.

Alternatively, a labeled ligand can be photoaffinity linked to a cell extract, such as a membrane or a membrane extract, prepared from cells that express a molecule that it binds, such as a binding molecule. Cross-linked material is resolved by polyacrylamide gel electrophoresis ("PAGE") and exposed to X-ray film. The labeled complex containing the ligand-binding can be excised, resolved into peptide fragments, and subjected to protein microsequencing. The amino acid sequence obtained from microsequencing can be used to design unique or degenerate oligonucleotide probes to screen cDNA libraries to identify genes encoding the putative binding molecule.

Polypeptides of the invention also can be used to assess cytokinin biosynthetic enzyme binding capacity of cytokinin biosynthetic enzyme binding molecules, such as binding molecules, in cells or in cell-free preparations.

Polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics.

Anti-cytokinin biosynthetic enzyme antibodies represent a useful class of binding molecules contemplated by this invention.

Antagonists and Agonists—Assays and Molecules

The invention also provides a method of screening compounds to identify those that enhance or block the action of cytokinin biosynthetic enzymes on cells, such as interaction with substrate molecules. An antagonist is a compound that decreases the natural biological functions of the enzymes. A particular enzyme to be targeted in this regard is cytokinin oxidase.

Potential antagonists include small organic molecules, peptides, polypeptides and antibodies that bind to cytokinin oxidase and thereby inhibit or extinguish its activity. Potential antagonists also may be small organic molecules, a peptide, a polypeptide such as a closely related protein or antibody, that binds the same sites on a binding molecule, such as a cytokinin oxidase binding molecule, without inducing cytokinin metabolic enzyme-induced activities, thereby preventing the action of the enzyme by excluding the enzyme from binding.

Potential antagonists include a small molecule that binds to and occupies the binding site of the polypeptide thereby preventing binding to cellular binding molecules, such as binding molecules, such that normal biological activity is prevented. Examples of small molecules include but are not limited to small organic molecules, peptides or peptide-like molecules.

Other potential antagonists include molecules that affect the expression of the gene encoding cytokinin biosynthetic enzymes (e.g. transactivation inhibitors). Other potential antagonists include antisense molecules. Antisense technology can be used to control gene expression through antisense DNA or RNA or through double- or triple-helix formation. Antisense techniques are discussed, for example, in—Okano, J. Neurochem. 56: 560 (1991); *OLIGODEOXY-NUCLEOTIDES AS ANTISENSE INHIBITORS OF GENE EXPRESSION*, CRC Press, Boca Raton, Fla. (1988). Triple helix formation is discussed in, for instance Lee et al., *Nucleic Acids Research* 6:3073 (1979); Cooney et al., *Science* 241:456 (1988); and Dervan et al., *Science* 251:1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription, thereby preventing transcription and the production of cytokinin biosynthetic enzymes. The antisense RNA oligonucleotide hybridizes to the mRNA in vivo and blocks translation of the mRNA molecule into cytokinin biosynthetic enzymes. The oligonucleotides described above can also be delivered to cells such that the antisense RNA or DNA may be expressed in vivo to inhibit production of cytokinin biosynthetic enzymes.

The DNAs of this invention may also be employed to co-suppress or silence the cytokinin metabolic enzyme genes; for example, as described in PCT Patent Application Publication WO 98/36083.

The antagonists may be employed for instance to increase the levels of cytokinin and/or decrease the available auxin in plant cells.

Alternatively, this invention provides methods for screening for agonists, those molecules that act to increase the natural biological function of enzymes. Targets in this regard include enzymes such ipt, β-glucosidase, and iaa-1.

Potential agonists include small organic molecules, peptides, polypeptides and antibodies that bind to a biosynthetic enzyme and thereby stimulate or increase its activity. Potential agonists also may be small organic molecules, a peptide, a polypeptide such as a closely related protein or antibody that binds to sites on a binding molecule, such as a ipt binding molecule and promotes cytokinin metabolic enzyme-induced activities, thereby enhancing the action of the enzyme.

Potential agonists include small molecules that bind to and occupy the allosteric sites of the enzyme thereby promoting binding to cellular binding molecules, such as substrates, such that normal biological activity is enhanced. Examples of small molecules include but are not limited to small organic molecules, peptides or peptide-like molecules.

Other potential agonists include molecules that affect the expression of the gene encoding cytokinin biosynthetic enzymes (e.g. transactivatiors).

EXAMPLES

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention. It will be obvious that certain changes and modifications may be practiced within the scope of the appended claims.

Certain terms used herein are explained in the foregoing glossary.

All examples were carried out using standard techniques, which are well known and routine to those of skill in the art, except where otherwise described in detail. Routine molecular biology techniques of the following examples can be carried out as described in standard laboratory manuals, such as Sambrook et al., *MOLECULAR CLONING: A LABORATORY MANUAL*, 2nd Ed.; Cold Spring Harbor Laboratory Press, Cold Spring Harbor, N.Y. (1989).

All parts or amounts set out in the following examples are by weight, unless otherwise specified.

Unless otherwise stated, size separation of fragments in the examples below was carried out using standard techniques of agarose and polyacrylamide gel electrophoresis ("PAGE") in Sambrook et al., *MOLECULAR CLONING: A LABORATORY MANUAL*, 2nd Ed., Cold Spring Harbor Laboratory Press, Cold Spring Harbor, N.Y. (1989) and numerous other references such as, for instance, by Goeddel et al., *Nucleic Acids Res.* 8:4057 (1980).

Unless described otherwise, ligations were accomplished using standard buffers, incubation temperatures and times, approximately equimolar amounts of the DNA fragments to be ligated and approximately 10 units of T4 DNA ligase ("ligase") per 0.5 microgram of DNA.

Example 1

Construction of Vectors System for Temporal and Spatial Seed Preferred Expression of Cytokinin Biosynthetic Enzymes Construction of PHP 11466 and PHP 11467 and their cointegrates (PHP11551 and PHP11552, respectively). PPH 11466 and PHP 11467 were employed in particle gun transformation protocols even though they have the right and left border for the tDNA. The versions designated PHP11551 and PHP11552 were used in Agro-mediated transformation protocols.

The ipt coding sequence was obtained as a 732 bp BamHI/Hpal fragment and inserted into a GLB1 expression cassette (BamHI/Hpal, 4.9 kb) to give PHP11310. The maize GLB1 promoter (Genbank Accession # L22344 L22295) and terminator (Genbank Accession # L22345 L22295) in PHP3303 comprise the GLB1 expression cassette. The pGLB1:ipt:GLB1 3' cassette was moved as two pieces (HindIII/BamHI 1401 bp and BamHI/EcoRI 1618 bp) into a T-DNA vector digested with EcoRI+HindIII (6.33 kb) to give PHP11363. Finally, a selectable marker gene (pUBI:UBIINTRON1:maize-optimized PAT:35S 3') was added as a 2.84 kb HindIII fragment into HindIII-digested PHP11363 (9.35 kb). In PHP11466, the two genes are in opposite orientation relative to each other. In PHP11467, the two genes are oriented in the same direction. After triparental mating the cointegrate of PHP11466/PHP10523 was designated PHP11551. Likewise, the cointegrate of PHP11467/PHP10523 was designated PHP11552.

Construction of PHP11404 and PHP11550.

PHP 11404 was used with the biolistics-mediated transformation protocol. The plasmid has all the features of the Agro version. The plasmid that was actually used with the Agro-mediated transformation protocols was is PHP11550.

Using the plasmid PHP9063 (pUBI:UBIINTRON1:ipt:pinII 3'), an NcoI restriction site was created at the start codon of ipt using site-directed mutagenesis (specifically, the MORPH™ Kit of 5 Prime→3 Prime, Inc.). The resulting plasmid was designated PHP11362. The ipt coding sequence was then moved as a 724 bp NcoI/Hpal fragment into PHP8001 (BamHI-cut, treated with Klenow to fill in the overhang to a blunt then cut with NcoI, 4.9 kb) to give PHP11401. PHP8001 contains the GZ-W64A promoter and terminator from the 27 KD zein gene of Z. mays (Genbank Accession # S78780). PHP11401 was digested with PacI+KpnI and a 1.35 kb fragment inserted into PHP11287 (PacI/KpnI-digested, 10.87 kb) to give PHP11404. PHP11287 is a T-DNA vector that already carries the above-described pUBI:UBIINTRON1:maize-optimized PAT:35S 3' selectable marker. After triparental mating the cointegrate of PHP11404/PHP10523 was designated PHP11550.

Construction of PHP12975

The CIM3 promoter is described in U.S. patent application Ser. No. 09/377,648, filed Aug. 19, 1999. Site-directed mutagenesis was used to create an NcoI site at the CIM1 translational start (PHP12699). The promoter was cut out as a 1.69 kb SacI/NcoI fragment and ligated to the ipt coding sequence and pinII terminator from PHP11362 to form PHP12800. The CIM1:ipt:pinII transcriptional unit was then moved as a 2.8 kb BstEII fragment into BstEII-digested PHP12515 (9.5 kb), a binary vector already carrying the UBI:UBIINTRON1:MO-PAT:35S selectable marker between the border sequences. The resulting plasmid was designated PHP12866. Triparental mating into *A. tumefaciens* LBA4404 (PHP10523) gave the cointegrate plasmid PHP12975.

Construction of PHP12425

Plasmid PHP11404 (described above) was used as a starting plasmid to replace the GZ-W64A promoter with the LTP2 promoter from *H. vulgare*. PHP11404 DNA was digested with NotI and KpnI (9.46 kb fragment) and separately with NcoI plus KpnI (1.24 kb fragment). These two fragments were mixed with a 1.52 kb NotI/NcoI fragment from PHP8219 containing the LTP2 promoter and ligated. The resulting plasmid product was designated PHP12333. Triparental mating of this plasmid into *A. tumefaciens* LBA4404 (PHP10523) gave the cointegrate plasmid PHP12425.

Triparental Mating and Selectable Marker 35s:bar:pinII:

All vectors were constructed using standard molecular biology techniques. The T-DNA region for transformation consists of the T-DNA border sequences flanking a reporter gene and a selectable marker. The reporter is inserted proximal to the right T-DNA border and consists of the 2.0 kb PstI fragment of the maize ubiquitin promoter Ubi-1 (Christensen et al., 1992) with flanking 5' HindIII and 3' BamHI restriction sites. The ubiquitin promoter was ligated to the 5' BamHI site of a beta-glucuronidase (GUS) reporter gene (Jefferson et al., 1986), containing the second intron from potato ST-LS1 (Vancanneyt et al., 1990). The potato proteinase II (pinII) terminator (bases 2 to 310 from An et al., Plant Cell 1(1):115–122 (1989)) was blunt-end ligated downstream of the GUS coding sequence. On the 3' end of the terminator is a NotI restriction site.

The selectable marker consists of an enhanced cauliflower mosaic virus 35S promoter (bases −421 to −90 and −421 to +2 from Gardner, R. C., et al., Nucl. Acids Res. 9:2871–88 (1981).)) with a flanking 5' NotI site and 3' PstI site. A PstI/SalI fragment containing the 79 bp tobacco mosaic virus leader (Gallie, D. R., et al., Nucl. Acids Res. 15:3257–73 (1987).)) is inserted downstream of the promoter followed by a SalI/BamHI fragment containing the first intron of maize alcohol dehydrogenase ADH1-S (Dennis et al., 1984). The BAR coding sequence (Thompson, C. J., et al., Embo J. 6:2519–23 (1987).)) was cloned into the BamHI site, with the pinII terminator ligated downstream. The pinII signal is flanked by a 3' SacI site.

The T-DNA of PHP8904 was integrated into the super binary plasmid pSB1 (Ishida et al. 1996) by homologous recombination between the two plasmids. *E. coli* strain HB101 containing PHP8904 was mated with *Agrobacterium* strain LBA4404 harboring pSB1 to create the cointegrate plasmid in *Agrobacterium* designated LBA4404 (PHP10525) (by the method Ditta, G., et al., Proc. Natl. Acad. Sci. USA 77:7347–51 (1980).) LBA4404(PHP10525) was selected for by *Agrobacterium* resistance to spectinomycin and verified as a recombinant by a SalI restriction digest of the plasmid.

Example 2

Transformation of Maize

Biolistics:

The inventive polynucleotides contained within a vector are transformed into embryogenic maize callus by particle bombardment, generally as described by Tomes, D. et al., IN: Plant Cell, Tissue and Organ Culture: Fundamental Methods, Eds. O. L. Gamborg and G. C. Phillips, Chapter 8, pgs. 197–213 (1995) and is briefly outlined below. Transgenic maize plants are produced by bombardment of embryogenically responsive immature embryos with tungsten particles associated with DNA plasmids. The plasmids consist of a selectable and an unselected structural gene.

Preparation of Particles:

Fifteen mg of tungsten particles (General Electric), 0.5 to 1.8μ, preferably 1 to 1.8μ, and most preferably 1μ, are added to 2 ml of concentrated nitric acid. This suspension was sonicated at 0° C. for 20 minutes (Branson Sonifier Model 450, 40% output, constant duty cycle). Tungsten particles are pelleted by centrifugation at 10000 rpm (Biofuge) for one minute, and the supernatant is removed. Two milliliters of sterile distilled water are added to the pellet, and brief sonication is used to resuspend the particles. The suspension is pelleted, one milliliter of absolute ethanol is added to the pellet, and brief sonication is used to resuspend the particles. Rinsing, pelleting, and resuspending of the particles is performed two more times with sterile distilled water, and finally the particles are resuspended in two milliliters of sterile distilled water. The particles are subdivided into 250-ml aliquots and stored frozen.

Preparation of Particle-Plasmid DNA Association:

The stock of tungsten particles are sonicated briefly in a water bath sonicator (Branson Sonifier Model 450, 20% output, constant duty cycle) and 50 ml is transferred to a microfuge tube. All the vectors were cis: that is the selectable marker and the gene of interest were on the same plasmid. These vectors were then transformed either singly or in combination.

Plasmid DNA was added to the particles for a final DNA amount of 0.1 to 10 μg in 10 μL total volume, and briefly sonicated. Preferably, 10 μg (1 μg/mL in TE buffer) total DNA is used to mix DNA and particles for bombardment. Specifically, 1.0 μg of PHP 11404, 11466, and/or 11467 (1 μg/μL), where any cytokinin biosynthetic enzyme polynucleotide can replace ipt were used per bombardment. Fifty microliters (50 μL) of sterile aqueous 2.5 M $CaCl_2$ are added, and the mixture is briefly sonicated and vortexed. Twenty microliters (20 μL) of sterile aqueous 0.1 M spermidine are added and the mixture is briefly sonicated and vortexed. The mixture is incubated at room temperature for 20 minutes with intermittent brief sohication. The particle suspension is centrifuged, and the supernatant is removed. Two hundred fifty microliters (250 μL) of absolute ethanol are added to the pellet, followed by brief sonication. The suspension is pelleted, the supernatant is removed, and 60 ml of absolute ethanol are added. The suspension is sonicated briefly before loading the particle-DNA agglomeration onto macrocarriers.

Preparation of Tissue

Immature embryos of maize variety High Type II are the target for particle bombardment-mediated transformation. This genotype is the $F_1$ of two purebred genetic lines, parents A and B, derived from the cross of two know maize inbreds, A188 and B73. Both parents are selected for high competence of somatic embryogenesis, according to Armstrong et al., *Maize Genetics Coop. News* 65:92 (1991).

Ears from $F_1$ plants are selfed or sibbed, and embryos are aseptically dissected from developing caryopses when the scutellum first becomes opaque. This stage occurs about 9–13 days post-pollination, and most generally about 10 days post-pollination, depending on growth conditions. The embryos are about 0.75 to 1.5 millimeters long. Ears are surface sterilized with 20–50% Clorox for 30 minutes, followed by three rinses with sterile distilled water.

Immature embryos are cultured with the scutellum oriented upward, on embryogenic induction medium comprised of N6 basal salts, Eriksson vitamins, 0.5 mg/l thiamine HCl, 30 gm/l sucrose, 2.88 gm/l L-proline, 1 mg/l 2,4-dichlorophenoxyacetic acid, 2 gm/l Gelrite, and 8.5 mg/l $AgNO_3$. Chu et al., *Sci. Sin.* 18:659 (1975); Eriksson, *Physiol. Plant* 18:976 (1965). The medium is sterilized by autoclaving at 121° C. for 15 minutes and dispensed into 100×25 mm Petri dishes. $AgNO_3$ is filter-sterilized and added to the medium after autoclaving. The tissues are cultured in complete darkness at 28° C. After about 3 to 7 days, most usually about 4 days, the scutellum of the embryo swells to about double its original size and the protuberances at the coleorhizal surface of the scutellum indicate the inception of embryogenic tissue. Up to 100% of the embryos display this response, but most commonly, the embryogenic response frequency is about 80%.

When the embryogenic response is observed, the embryos are transferred to a medium comprised of induction medium modified to contain 120 gm/l sucrose. The embryos are oriented with the coleorhizal pole, the embryogenically responsive tissue, upwards from the culture medium. Ten embryos per Petri dish are located in the center of a Petri dish in an area about 2 cm in diameter. The embryos are maintained on this medium for 3–16 hour, preferably 4 hours, in complete darkness at 28° C. just prior to bombardment with particles associated with plasmid DNAs containing the selectable and unselectable marker genes.

To effect particle bombardment of embryos, the particle-DNA agglomerates are accelerated using a DuPont PDS-1000 particle acceleration device. The particle-DNA agglomeration is briefly sonicated and 10 ml are deposited on macrocarriers and the ethanol is allowed to evaporate. The macrocarrier is accelerated onto a stainless-steel stopping screen by the rupture of a polymer diaphragm (rupture disk). Rupture is effected by pressurized helium. The velocity of particle-DNA acceleration is determined based on the rupture disk breaking pressure. Rupture disk pressures of 200 to 1800 psi are used, with 650 to 1100 psi being preferred, and about 900 psi being most highly preferred. Multiple disks are used to effect a range of rupture pressures.

The shelf containing the plate with embryos is placed 5.1 cm below the bottom of the macrocarrier platform (shelf #3). To effect particle bombardment of cultured immature embryos, a rupture disk and a macrocarrier with dried particle-DNA agglomerates are installed in the device. The He pressure delivered to the device is adjusted to 200 psi above the rupture disk breaking pressure. A Petri dish with the target embryos is placed into the vacuum chamber and located in the projected path of accelerated particles. A vacuum is created in the chamber, preferably about 28 in Hg. After operation of the device, the vacuum is released and the Petri dish is removed.

Bombarded embryos remain on the osmotically-adjusted medium during bombardment, and 1 to 4 days subsequently. The embryos are transferred to selection medium comprised of N6 basal salts, Eriksson vitamins, 0.5 mg/1 thiamine HCl, 30 gm/l sucrose, 1 mg/l 2,4-dichlorophenoxyacetic acid, 2 gm/l Gelrite, 0.85 mg/l Ag $NO_3$ and 3 mg/l bialaphos (Herbiace, Meiji). Bialaphos is added filter-sterilized. The embryos are subcultured to fresh selection medium at 10 to 14 day intervals. After about 7 weeks, embryogenic tissue, putatively transformed for both selectable and unselectable marker genes, proliferates from about 7% of the bombarded embryos. Putative transgenic tissue is rescued, and that tissue derived from individual embryos is considered to be an event and is propagated independently on selection medium. Two cycles of clonal propagation are achieved by visual selection for the smallest contiguous fragments of organized embryogenic tissue.

A sample of tissue from each event is processed to recover DNA. The DNA is restricted with a restriction endonuclease and probed with primer sequences designed to amplify DNA sequences overlapping the cytokinin biosynthetic enzymes and non-cytokinin biosynthetic enzyme portion of the plasmid. Embryogenic tissue with amplifiable sequence is advanced to plant regeneration.

For regeneration of transgenic plants, embryogenic tissue is subcultured to a medium comprising MS salts and vitamins (Murashige & Skoog, *Physiol. Plant* 15: 473 (1962)), 100 mg/l myo-inositol, 60 gm/l sucrose, 3 gm/l Gelrite, 0.5 mg/l zeatin, 1 mg/l indole-3-acetic acid, 26.4 ng/l cis-trans-abscissic acid, and 3 mg/l bialaphos in 100×25 mm Petri dishes, and is incubated in darkness at 28° C. until the development of well-formed, matured somatic embryos can be seen. This requires about 14 days. Well-formed somatic embryos are opaque and cream-colored, and are comprised of an identifiable scutellum and coleoptile. The embryos are individually subcultured to a germination medium comprising MS salts and vitamins, 100 mg/l myo-inositol, 40 gm/l sucrose and 1.5 gm/l Gelrite in 100×25 mm Petri dishes and incubated under a 16 hour light:8 hour dark photoperiod and 40 meinsteinsm$^{-2}$ sec$^{-1}$ from cool-white fluorescent tubes. After about 7 days, the somatic embryos have germinated and produced a well-defined shoot and root. The individual plants are subcultured to germination medium in 125×25 mm glass tubes to allow further plant development. The plants are maintained under a 16 hour light:8 hour dark photoperiod and 40 meinsteinsm$^{-2}$ sec$^{-1}$ from cool-white fluorescent tubes. After about 7 days, the plants are well-established and are transplanted to horticultural soil, hardened off, and potted into commercial greenhouse soil mixture and grown to sexual maturity in a greenhouse. An elite inbred line is used as a male to pollinate regenerated transgenic plants.

*Agrobacterium*-Mediated:

When *Agrobacterium*-mediated transformation is used, the method of Zhao is employed as in PCT patent publication WO98/32326, the contents of which are hereby incorporated by reference. Briefly, immature embryos are isolated from maize and the embryos contacted with a suspension of *Agrobacterium* (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step) and preferably calli grown on selective medium are cultured on solid medium to regenerate the plants.

Example 3

Identification of High Cytokinin Transgenic Corn Lines

The resulting transformants are screened for elevated levels of cytokinin using a combination of direct measurements and in vivo correlates.

Vivipary Experiments (lb1:ipt constructs):

Because it is appreciated that seed dormancy is controlled by the ratio of ABA:cytokinin, an elevated cytokinin level in the seed could induce a viviparous phenotype.

Glb1::ipt transformants were initiated using GS3 embryos and either *Agrobacterium*-(inventive polynucleotides 11551 and 11552) or biolistic-(inventive polynucleotides 11466 and 11467) mediated transformation. Plantlets were regenerated 2–3 months later and these plantlets (T0's) were transferred to the greenhouse after an additional 2–3 months. At anthesis, T0's were crossed with HG11 and vivipary was detected in the developing T1 seed approximately 30 days later. Developing T1 seed that exhibited the viviparous phenotype was rescued by replanting without seed drying. Viable plants were analyzed by PCR and leaf-painting to determine if the ipt gene and the selectable marker (PAT gene) were present. T1 plants flowered and ears were selfed to create T2 seed. Those plants carrying the ipt gene (PCR- and leaf paint-positive) produced seed that were segregating 3:1 for the gene, whereas the plants that were PCR- and leaf paint-negative did not segregate.

Cytokinin Determinations:

At 19 and 23 days after pollination (DAP), ten seeds were harvested from each of four replications per event (11551 and 11552). Seeds were then separated into embryo and endosperm and frozen in liquid nitrogen. At each sampling date, embryo tissue from the four replications was pooled and cytokinin levels were determined. Endosperm tissue was processed in an similar manner. The results are presented in FIG. 1.

qlb1::ipt Seed Propagation:

In order to propagate the viviparous seed, half of the remaining plants within each event were harvested at 25 DAP. Ears were placed in dryer boxes and ambient air (22 to 25 C) was blown across them for three days to slowly dry the seed. Dryer boxes containing the transgenic ears were then transferred to a growth chamber and seeds were dried to ~12% moisture by blowing 35C air across them for 3 to 5 days. Individual ears were then shelled and the seeds stored at 10C and 50% RH.

Phenotype Determination:

To determine the proportion of seed exhibiting vivipary, ears from the remaining half of the plants were harvested at approximately 45 DAP and seed scored for degree of vivipary. The four classes of vivipary were defined as:

Class 1: No apparent swelling of coleoptile.
Class 2: Visible swelling of coleoptile, but no elongation.
Class 3: Visible swelling of coleoptile with elongation past the scutellum, but no rupture of pericarp.
Class 4: Visible swelling of coleoptile with elongation past the scutellum and rupture of pericarp.

The results are shown below in Table 1.

TABLE 1

| Event | SID # | PCR Result | Leaf Paint Result | T2 Phenotype Vivipary Result | Vivipary Characterization at 45 DAP | | | | Total Seed # |
|---|---|---|---|---|---|---|---|---|---|
| | | | | | Class 1 | Class 2 | Class 3 | Class 4 | |
| 11551 | 751412 | + | + | + | 4 | 4 | 7 | 4 | 19 |
| | 751415 | + | + | + | 0 | 169 | 34 | 2 | 205 |
| | 751416 | + | + | + | 99 | 28 | 18 | 59 | 204 |
| | 751417 | + | + | + | 167 | 55 | 39 | 18 | 279 |
| | 751420 | + | + | + | 2 | 193 | 47 | 0 | 242 |
| | 751422 | + | + | + | 0 | 141 | 93 | 11 | 245 |
| | Sum | | | | 272 | 590 | 238 | 94 | 1194 |
| 11551 | 751425 | + | + | + | 50 | 57 | 85 | 4 | 196 |
| | 751426 | + | + | + | 0 | 75 | 64 | 12 | 151 |
| | 751429 | + | + | + | 66 | 40 | 19 | 4 | 129 |
| | 751432 | + | + | + | 41 | 16 | 14 | 4 | 75 |
| | Sum | | | | 157 | 188 | 182 | 24 | 551 |
| 11551 | 751433 | − | − | | | | | | |
| | 751434 | − | − | − | 438 | 0 | 0 | 0 | 438 |
| | 751435 | − | − | − | 405 | 0 | 0 | 0 | 405 |
| | 751436 | − | − | − | 375 | 0 | 0 | 0 | 375 |
| | Sum | | | | 406 | 0 | 0 | 0 | 406 |
| 11551 | 751437 | + | + | + | 14 | 50 | 78 | 19 | 161 |
| | 751438 | − | + | + | 52 | 37 | 128 | 10 | 227 |
| | 751439 | + | + | + | 128 | 92 | 101 | 9 | 330 |
| | 751443 | + | + | + | 70 | 84 | 89 | 4 | 247 |
| | Sum | | | | 264 | 263 | 396 | 42 | 965 |
| 11551 | 751441 | − | − | − | 375 | 0 | 0 | 0 | 375 |
| | 751442 | + | − | | | | | | |
| | 751444 | − | − | − | 343 | 0 | 0 | 0 | 343 |
| | Sum | | | | 359 | 0 | 0 | 0 | 359 |
| 11551 | 751445 | | | + | 158 | 76 | 38 | 9 | 281 |
| | 751448 | − | + | + | 4 | 126 | 79 | 3 | 212 |
| | 751450 | + | + | + | 101 | 83 | 44 | 14 | 242 |
| | 751451 | + | + | + | 101 | 33 | 48 | 1 | 183 |
| | Sum | | | | 364 | 318 | 209 | 27 | 918 |
| 11552 | 752902 | | + | + | 16 | 53 | 62 | 4 | 135 |
| | 752908 | + | + | + | 35 | 74 | 24 | 4 | 137 |
| | 752910 | + | + | + | 9 | 132 | 14 | 0 | 155 |
| | 752911 | + | + | + | 2 | 148 | 39 | 3 | 192 |
| | 752912 | + | + | + | 0 | 40 | 27 | 2 | 69 |
| | 752913 | + | + | + | 49 | 36 | 36 | 8 | 129 |
| | 752914 | + | + | + | 75 | 47 | 12 | 21 | 155 |
| | 752919 | | + | + | 25 | 72 | 80 | 16 | 193 |
| | Sum | | | | 211 | 602 | 294 | 58 | 1165 |
| 11551 | 752924 | + | + | + | 109 | 57 | 98 | 16 | 280 |
| | 752930 | + | + | + | 6 | 27 | 22 | 10 | 65 |
| | 752936 | + | + | + | 53 | 60 | 47 | 3 | 163 |
| | 752937 | + | + | + | 53 | 36 | 70 | 10 | 169 |
| | 752939 | + | + | + | 58 | 48 | 68 | 6 | 180 |
| | 752940 | + | + | | 0 | 1 | 0 | 0 | |
| | Sum | | | | 279 | 229 | 305 | 45 | 857 |

The results of the phenotypic evaluation demonstrated that the presence of the ipt gene resulted in a greater occurrence of vivipary (Classes 2 through 4), relative to the plants without the gene.

Increased Seed Dry Unit Mass (qz:ipt constructs):

Because kernel mass is a function of the number of endosperm cells and amyloplasts, and cytokinins have been implicated in increasing endosperm cell number and in the differentiation of amyloplasts from proplastids, seeds exhibiting an increased level of cytokinin should yield a corresponding increase in seed dry unit mass.

Gz::ipt transformants were initiated using GS3 embryos and *Agrobacterium*-mediated transformation (inventive polynucleotide 11550). Plantlets were regenerated in 2–3 months in 1997 and these plantlets (T0's) were transferred to the greenhouse after an additional 2–3 months. At anthesis, T0's were crossed with HG11 and at maturity the ears were harvested, shelled and the seed used for additional seed propagation (both backcrossing to HG11 and self-pollinating). T2 seed (both BC2 generation and selfs) was then planted. The T2 plants were analyzed by using PCR and leaf painting to determine if the ipt gene and the selectable marker (PAT gene) were present, respectively. Subsets of these plants were self-pollinated for cytokinin determinations, or allowed to open pollinate for phenotype determinations (yield and yield components).

Cytokinin Determinations:

Samples can be collected and analyzed as follows. At 10, 16 and 22 DAP, 50 to 100 seeds can be collected from two replications per event (each replication was composed of two subsamples) and the pedicel removed. For the 10 DAP samples, the remaining seed tissue can be placed directly into liquid nitrogen (tissue defined as "seed," composed primarily of pericarp, aleurone, endosperm and nucellus). In contrast, at 16 and 22 DAP, the embryo can be first dissected from the remaining seed tissue (tissue defined as "seed minus embryo," and composed primarily of pericarp, aleurone and endosperm) and then both tissues placed directly into liquid nitrogen.

Phenotype Determination:

To determine the effect of the gz::ipt construct on seed mass, individual plants are hand harvested at physiological maturity (visible black layer), the seed shelled and oven dried to a constant mass (104 C, minimum of 3 days). Yield (g plant) and the components of yield (ears per plant, seeds per ear and wt per seed) are determined on primary and secondary ears.

Increased Frequency of Seed Set and Increased Number of Seeds (lpt2:ipt Constructs):

Because yield is a combination of both frequency of seed set and number of seeds per ear, seeds exhibiting an increased level of cytokinin in the early stages of seed set and formation should have ears with a corresponding increase in seed set and numbers.

Lpt2::ipt transformants were initiated using GS3 embryos and *Agrobacterium*-mediated transformation (12425). Plantlets were regenerated in 2–3 months in 1998 and these plantlets (T0's) were transferred to the greenhouse after an additional 2–3 months. At anthesis, T0's were crossed with HG11 and at maturity the ears were harvested, shelled and the seed used for additional seed propagation (both backcrossing to HG11 and self-pollinating). The number of seeds per T0 event, and the number of events which set seed were compared to a number of other transgenic events with promoter:gene combinations other than ltp2:ipt. These are shown in Table 2.

TABLE 2

Seed set average of T0 events of ltp2:ipt gene compared to other genes in T0 plants grown under identical green house conditions in 1998 in Johnston, IA.

| Inventive polynucleotide | gene description | number T0's | % T0 w/ seed | average # seeds |
|---|---|---|---|---|
| 12425 | ltp2:ipt | 35 | 82.9 | 198 |
| 12384 | lignin | 92 | 22.8 | 145 |
| 12417 | carbohydrate | 40 | 55.0 | 156 |
| 12427 | maturity | 35 | 45.7 | 69 |
| 12428 | lignin | 29 | 75.9 | 174 |
| 12723 | lignin | 35 | 62.9 | 184 |
| 12724 | lignin | 35 | 45.7 | 161 |

Compared to % seed set and average # seeds per T0 plant, lpt2:ipt, had both the highest % of T0 plants which set seed and the highest numerical average # of seeds compared to six other transgenic combinations in T0 plants grown at the same time and under the same greenhouse conditions. These results indicate that expression of cytokinin in the aleurone layer of early seed development may increase yield by increasing both the percentage of plants that set seed, and the number of seeds set per ear.

Subsequent generations will be grown at different field locations to determine their seed set and seed number characteristics and seed yield compared to non-transgenic controls of the same genetic background. Cytokinin levels will also be measured on transgenic and non-transgenic kernels of similar genetic background.

Cytokinin Determinations:

Samples can be collected and analyzed as follows. At 2, 6 and 22 DAP, 50 to 100 seeds can be collected from two replications per event (each replication composed of two subsamples) and the pedicel removed. For the 2, 6, and 22 DAP samples, the remaining seed tissue can be placed directly into liquid nitrogen (tissue defined as "seed," composed primarily of pericarp, aleurone, endosperm and nucellus).

Sequence Descriptions:

SEQ ID NO.: 1 cytox1–2 (maize cytokinin oxidase)

SEQ ID NO.:2

Amino Acid sequence of cytox1–2

SEQ ID NO.: 3

Primer for isolation of ipt gene

SEQ ID NO.: 4

Primer for isolation of ipt gene

SEQ ID NO.: 5

Primer for isolation of cytokinin oxidase gene

SEQ ID NO.: 6

Primer for isolation of cytokinin oxidase gene

SEQ ID NO.: 7 gzw64a: ipt: gzw64a term

SEQ ID NO.: 8 ltp2: ipt: gzw64a term

SEQ ID NO.: 9 cim1: ipt: pinII

SEQ ID NO.: 10 ipt probe

SEQ ID NO.: 11 ipt probe

SEQ ID NO.: 12 gib1: ipt: gib1 term

What is claimed is:

1. A method for producing transgenic plants comprising: transforming plant host cells with a genetic construct, said construct comprising a seed preferred or seed specific promoter driving expression in developing seeds, wherein said promoter is operably linked to an isolated polynucleotide encoding an isopentenyl transferase, wherein the isolated polynucleotide is expressed in the transformed plant cells; and regenerating transgenic plants from said transformed plant cells, wherein said plants exhibit one or more traits selected from the group consisting of increased seed size, and increased seed number relative to a plant not transformed with said construct.

2. The method according to claim 1 wherein transforming is by a process selected from the group consisting of electroporation, PEG poration, particle bombardment, silicon fiber delivery, microinjection, and *Agrobacterium*-mediated transformation.

3. The method according to claim 2 wherein said process is particle bombardment.

4. The method according to claim 2 wherein said process is *Agrobacterium*-mediated transformation.

5. The method according to claim 1 wherein said promoter directs embryo-preferred expression.

6. A transgenic plant comprising a genetic construct stably integrated into the genome thereof, said construct comprising a seed preferred or seed specific promoter driving expression in developing seeds, wherein said promoter is operably linked to an isolated polynucleotide encoding an isopentenyl transferase, and wherein said plant exhibits one or more traits selected from the group consisting of increased seed size, and increased seed number relative to a plant not transformed with said construct.

7. The plant according to claim 6 wherein said promoter directs embryo-preferred expression.

8. An isolated recombinant DNA molecule comprising a seed preferred or seed specific promoter, wherein said promoter is operably linked to an isolated polynucleotide encoding an isopentenyl transferase.

9. The DNA molecule according to claim 8 wherein said promoter directs embryo-preferred expression.

10. Host plant cells comprising the DNA molecule of claim 8.

11. A method for increasing seed number and/or seed size comprising stably transforming plant host cells with a genetic construct, said construct comprising a seed preferred or seed specific promoter driving expression in developing seeds, wherein said promoter is operably linked to an isolated polynucleotide encoding an isopentenyl trasferase, and regenerating plants from said cells, wherein the introduced DNA is expressed in seed of the transformed plants and said plants exhibit an increase in seed number and/or seed size compared to plants not transformed with said construct.

12. The method according to claim 11 wherein said seed expression is initiated within the range of from about 14 days prior to pollination to about 25 days after pollination.

13. The method according to claim 11 wherein said seed expression is initiated within the range of from about 14 days prior to about 21 days after pollination.

14. The method according to claim 11 wherein said seed expression is initiated within the range of from about 14 days prior to about 12 days after pollination.

15. The method according to claim 11 wherein said seed expression is initiated within the range of from about 14 days prior to pollination to zero days after pollination.

16. A method for producing transgenic plants having increased cytokinin content in developing seeds compared to an untransformed plant comprising: transforming plant host cells with a genetic construct, said construct comprising a seed preferred or seed specific promoter driving expression in developing seeds, wherein said promoter is operably linked to an isolated polynucleotide encoding an isopentenyl transferase, and wherein the isolated polynucleotide is expressed in the transformed plant cells; regenerating plants from said transformed cells; and selecting plants with increased cytokinin content in seeds, compared to seeds of a plant not transformed with said construct by selecting plants with viviparous seed.

17. A method for producing transgenic plants wherein cytokinin content, in developing seeds is increased relative to a non-transgenic plant comprising: transforming plant host cells with a genetic construct, said construct comprising a seed preferred or seed specific promoter driving expression in developing seeds operably linked to an isolated polynucleotide encoding an isopentenyl transferase, wherein said construct further comprises an isolated polynucleotide encoding a selectable marker, and wherein the isolated polynucleotides are expressed in the transformed plant cells; regenerating plants from said transformed cells; and selecting plants with increased cytokinin content in seeds by screening for the presence of the selectable marker.

* * * * *